(12) United States Patent
Fallin et al.

(10) Patent No.: US 11,903,840 B2
(45) Date of Patent: Feb. 20, 2024

(54) FUSION IMPLANT

(71) Applicant: Smith & Nephew, Inc., Memphis, TN (US)

(72) Inventors: T. Wade Fallin, Hyde Park, UT (US); M. Mary Sinnott, Logan, UT (US); Patrick Michel White, West Chester, PA (US)

(73) Assignee: Smith & Nephew, Inc., Memphis, TN (US)

( * ) Notice: Subject to any disclaimer, the term of this patent is extended or adjusted under 35 U.S.C. 154(b) by 809 days.

(21) Appl. No.: 16/859,279

(22) Filed: Apr. 27, 2020

(65) Prior Publication Data

US 2020/0261234 A1 Aug. 20, 2020

Related U.S. Application Data

(62) Division of application No. 13/845,544, filed on Mar. 18, 2013, now Pat. No. 10,631,994.

(60) Provisional application No. 61/713,471, filed on Oct. 12, 2012.

(51) Int. Cl.
| | |
|---|---|
| *A61F 2/42* | (2006.01) |
| *A61B 17/86* | (2006.01) |
| *A61B 17/72* | (2006.01) |
| *A61B 17/88* | (2006.01) |
| *A61B 17/68* | (2006.01) |
| *A61B 17/56* | (2006.01) |

(52) U.S. Cl.
CPC ........ *A61F 2/4241* (2013.01); *A61B 17/7291* (2013.01); *A61B 17/8685* (2013.01); *A61F 2/4225* (2013.01); *A61B 17/562* (2013.01); *A61B 17/686* (2013.01); *A61B 17/863* (2013.01); *A61B 17/8645* (2013.01); *A61B 17/8875* (2013.01); *A61B 17/8888* (2013.01); *A61B 2017/564* (2013.01); *A61F 2002/4228* (2013.01)

(58) Field of Classification Search
CPC . A61B 17/84; A61B 17/7291; A61B 17/8685; A61B 17/8888; A61B 2017/564; A61F 2/4225; A61F 2/4241; A61F 2002/4235; A61F 2002/423
USPC ................................................ 606/308, 328
See application file for complete search history.

(56) References Cited

U.S. PATENT DOCUMENTS

| | | |
|---|---|---|
| 184,718 A | 11/1876 | Lewis |
| 2,570,465 A | 10/1951 | Lundholm |
| 3,103,926 A | 9/1963 | Cochran et al. |
| 3,522,830 A | 8/1970 | Blizard |
| 3,744,488 A | 7/1973 | Cox |

(Continued)

FOREIGN PATENT DOCUMENTS

| | | |
|---|---|---|
| WO | 2010096724 A1 | 8/2010 |
| WO | 2011130229 A1 | 10/2011 |

(Continued)

OTHER PUBLICATIONS

ARROW-LOK Hybrid Catalog, 1 pg.

(Continued)

*Primary Examiner* — Marcela I. Shirsat
(74) *Attorney, Agent, or Firm* — Taft Stettinius & Hollister LLP

(57) ABSTRACT

Implants, instruments, and methods are presented for fixing adjacent bone portions to promote fusion of the bone portion.

20 Claims, 21 Drawing Sheets

(56) References Cited

U.S. PATENT DOCUMENTS

| | | | |
|---|---|---|---|
| 4,463,753 | A | 8/1984 | Gustilo |
| 5,417,692 | A | 5/1995 | Goble et al. |
| 5,571,139 | A | 11/1996 | Jenkins, Jr. |
| 5,643,267 | A | 7/1997 | Hitomi et al. |
| 5,766,250 | A | 6/1998 | Chervitz et al. |
| 5,782,918 | A | 7/1998 | Klardie et al. |
| 5,827,285 | A | 10/1998 | Bramlet |
| 5,919,193 | A | 7/1999 | Slavitt |
| 5,931,840 | A | 8/1999 | Goble et al. |
| 6,203,545 | B1 | 3/2001 | Stoffella |
| 6,413,260 | B1 | 7/2002 | Berrevoets et al. |
| 6,458,134 | B1 | 10/2002 | Songer et al. |
| 6,517,543 | B1 | 2/2003 | Berrevoets et al. |
| 6,616,694 | B1 | 9/2003 | Hart |
| 6,863,072 | B1 | 3/2005 | Sinnott et al. |
| 6,890,333 | B2 | 5/2005 | Von Hoffmann et al. |
| 7,004,702 | B2 | 2/2006 | Van Der Heijden |
| 7,041,106 | B1 | 5/2006 | Carver et al. |
| 7,044,953 | B2 | 5/2006 | Capanni |
| 7,144,413 | B2 | 12/2006 | Wilford et al. |
| 7,175,626 | B2 | 2/2007 | Neff |
| 7,635,364 | B2 | 12/2009 | Barrall et al. |
| 7,637,949 | B2 | 12/2009 | Hart |
| 7,641,677 | B2 | 1/2010 | Weiner et al. |
| 7,794,483 | B2 | 9/2010 | Capanni |
| 7,951,198 | B2 * | 5/2011 | Sucec ............ A61F 2/4261 606/328 |
| 8,048,134 | B2 | 11/2011 | Partin |
| 8,070,491 | B2 | 12/2011 | Mundwiler et al. |
| 8,083,521 | B2 | 12/2011 | Baughman et al. |
| 8,100,969 | B2 | 1/2012 | Hart |
| 8,100,983 | B2 | 1/2012 | Schulte |
| 8,303,307 | B2 | 11/2012 | Mundwiler et al. |
| 9,072,562 | B2 | 7/2015 | Weiner et al. |
| 2004/0097943 | A1 | 5/2004 | Hart |
| 2004/0167519 | A1 | 8/2004 | Weiner et al. |
| 2008/0177262 | A1 | 7/2008 | Augoyard et al. |
| 2009/0210016 | A1 | 8/2009 | Champagne |
| 2009/0248089 | A1 * | 10/2009 | Jacofsky ............ A61B 17/8685 606/86 R |
| 2010/0036439 | A1 | 2/2010 | Lavi |
| 2011/0004255 | A1 | 1/2011 | Weiner et al. |
| 2011/0082508 | A1 | 4/2011 | Reed |
| 2011/0257652 | A1 | 10/2011 | Roman |
| 2012/0065692 | A1 | 3/2012 | Champagne et al. |
| 2013/0030475 | A1 | 1/2013 | Weiner et al. |
| 2013/0165982 | A1 * | 6/2013 | Ek ............ A61B 17/84 606/328 |
| 2013/0274814 | A1 * | 10/2013 | Weiner ............ A61B 17/7291 606/301 |

FOREIGN PATENT DOCUMENTS

| | | | | |
|---|---|---|---|---|
| WO | WO-2012055999 | A1 * | 5/2012 | ............ A61F 2/4225 |
| WO | 2012103335 | A1 | 8/2012 | |

OTHER PUBLICATIONS

Ascension Total Foot System, MPJ Fusion Surgical Technique; Austin, TX; Ascension Orthopedics, Inc., 2009; LC-04-897-005 Rev A; 4 pages.

AutoFIX 2.0/2.5mm Cannulated Compression Screws Surgical Technique; Morrisville, PA; Small Bone Innovations, Inc.; MKT 3041 Rev. A; 4 pages.

BioPro HBS Headless Bone Screw; Port Huron, MI; BioPro, Brochure No. 18675 Rev. 2; 4 pages.

Blitz et al.; Plantar Plate Repair of the Second Metatarsophalangeal Joint: Technique and Tips; Journal of Foot & Ankle Surgery; 2004 43(4); 266-270.

Coughlin et al.; Second MTP Joint Instability: Grading of the Deformity and Description of Surgical Repair of Capsular Insufficiency; The Physician and Sportmedicine; Sep. 3, 2011; 39(3); 132-141.

DigiFuse Cannulated Intramedullary Fusion System; Houston, TX; Metasurg; 2012; P/N 100154; Rev. E.; 4 pages.

Fleming and Camasta; Plantar Plate Dysfunction; Chapter 4; 2002; pp. 22-28; http://www.podiatryinstitute.com/pdfs/Update_2002/2002_04.pdf.

Foot and Ankle Solutions Brochure; Zimmer; 2005; 24 pages; 97-4902-101-00.

Gregg et al.; Plantar Plate Repair and Weil Osteotomy for Metatarsophalangeal Joint Instability; Foot and Ankle Surgery; 2007; 13:116-121.

Hammertoe Fusion Set; Hillsboro, OR; ACUMED; 2010; 8 pages.

Hammertoe PIP Joint Arthodesis Using Trim-It Spin Pin Fixation; Arthrex, Inc.; 2011; LT0459B; 4 pages; www.arthrex.com.

IPP-ON Interphalangeal Implant; Saint Priest, France; Integra LifeSciences Services (France) SAS; Copyright 2009 ILS 06-07-053-02-09; 8 pages.

Nery et al.; Lesser Metatarsophalangeal Joint Instability: Prospective Evaluation and Repair of Plantar Plate and Capsular Insufficiency; Foot and Ankle International; Apr. 2012; vol. 33(4):301-311.

NexFix MTP Fusion System Anatomic Design for First MTP Arthrodesis; Edina, MN; Tornier, Copyright 2011; 6 pages.

Pro-Toe VO Hammertoe Fixation System Surgical Technique; Arlington, TN; Wright Medical Technology, Inc.; 2013; FA196-410 R113; 20 pages.

Smart Toe Intramedullary Shape Memory Implant; Memphis, TN; MMI-USA; 2009; SMT1000-rev. E; 2 pages.

Spin Snap-Off Screw Surgical Technique; Plainsboro, NJ; Integra LifeSciences Corporation; 2009; 4 pages.

StayFuse: Tips and Tricks; Nexa Orthopedics; 4 pages.

StayFuse Intramedullary Fusion Device for Hammertoe Deformity; San Diego, CA: Nexa Orthopedics; Copyright 2004-2006; #19-5054 Rev. B; 4 pages.

Weil et al.; Anatomic Plantar Plate Repair Using the Weil Metatarsal Osteotomy Approach; Foot and Ankle Specialist; Jun. 22, 2011; 4:145-150; Originally published online on Mar. 18, 2011; http://fas.sagepub.com/content/4/3/145.

* cited by examiner

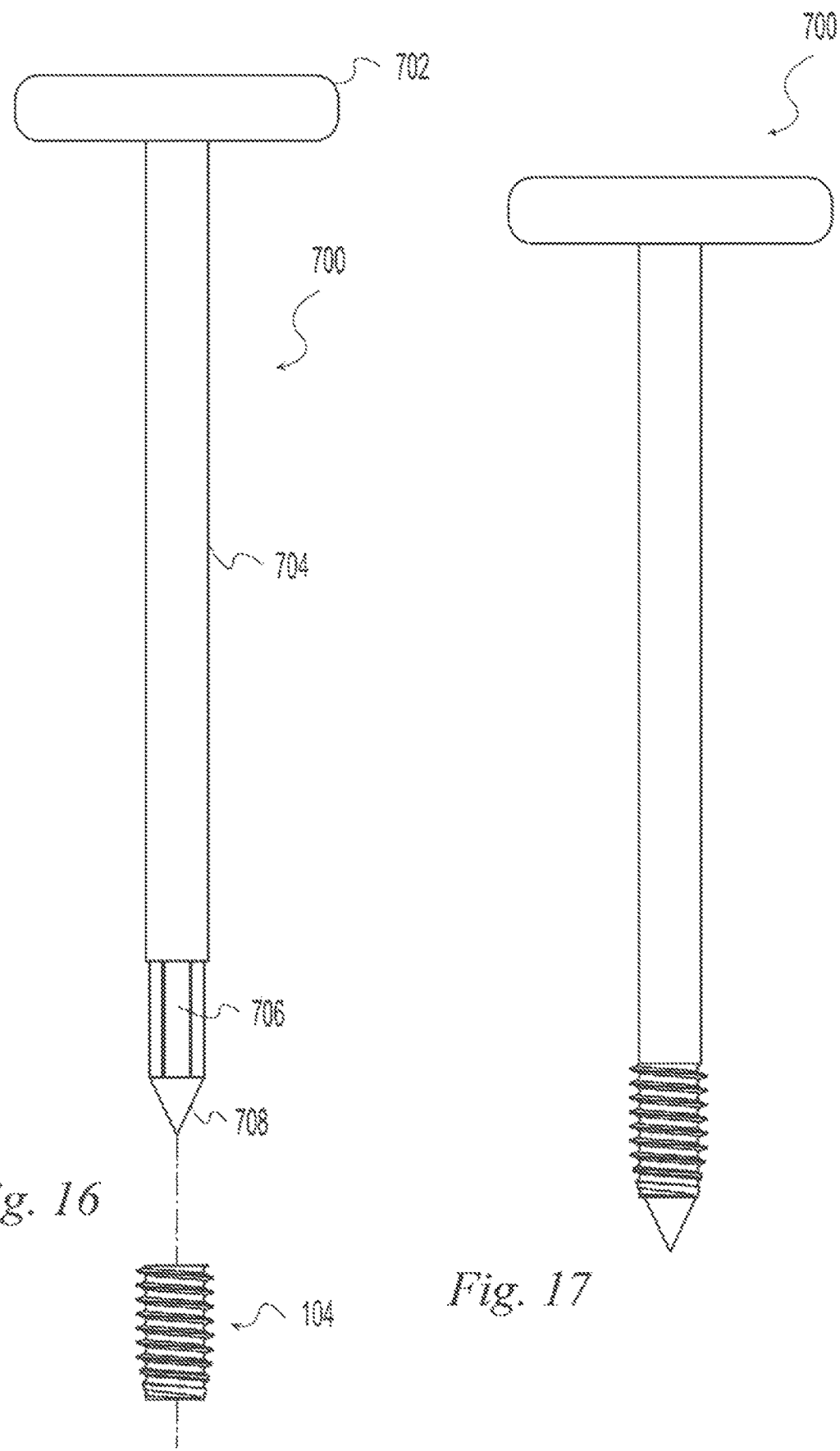

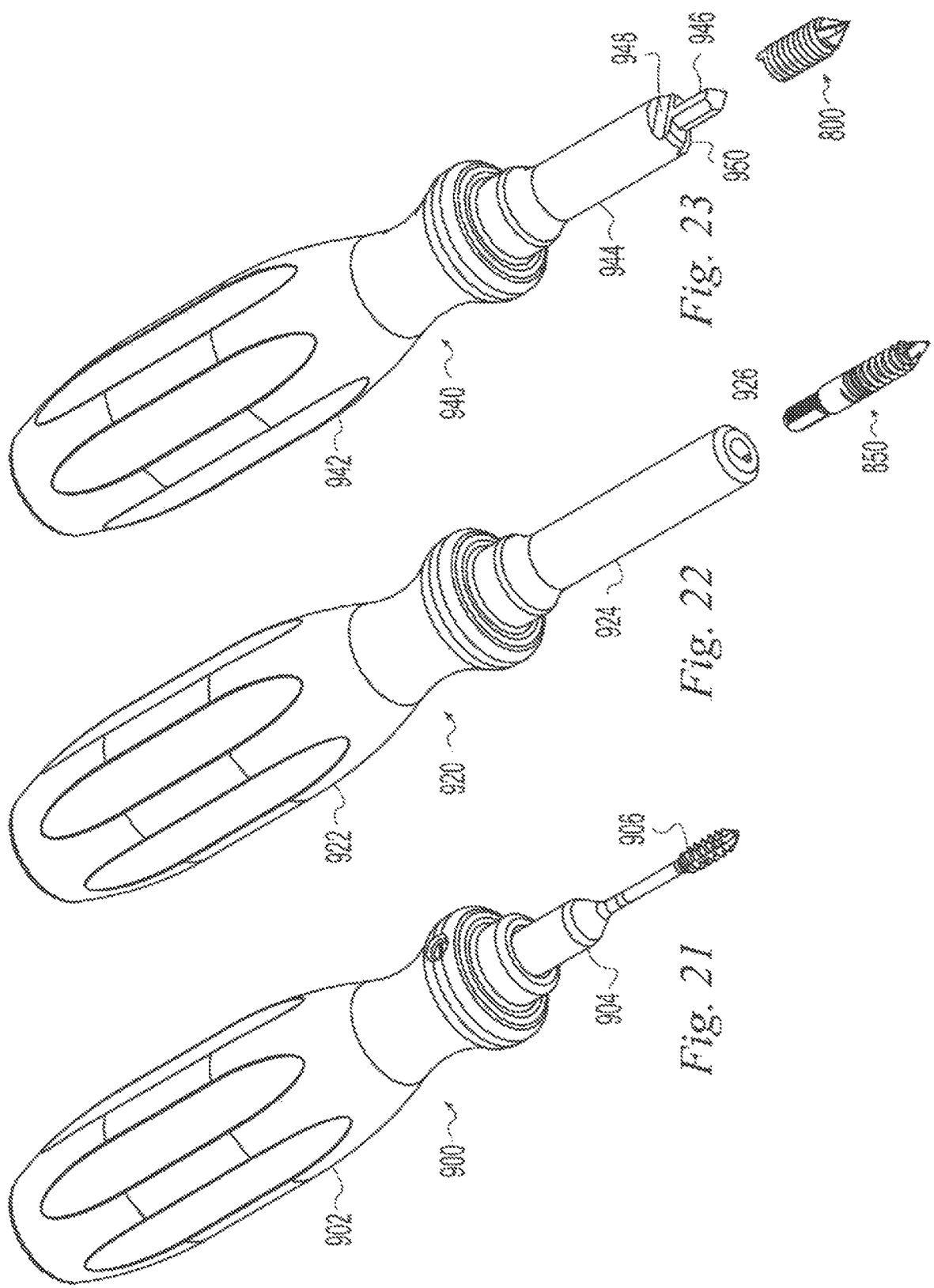

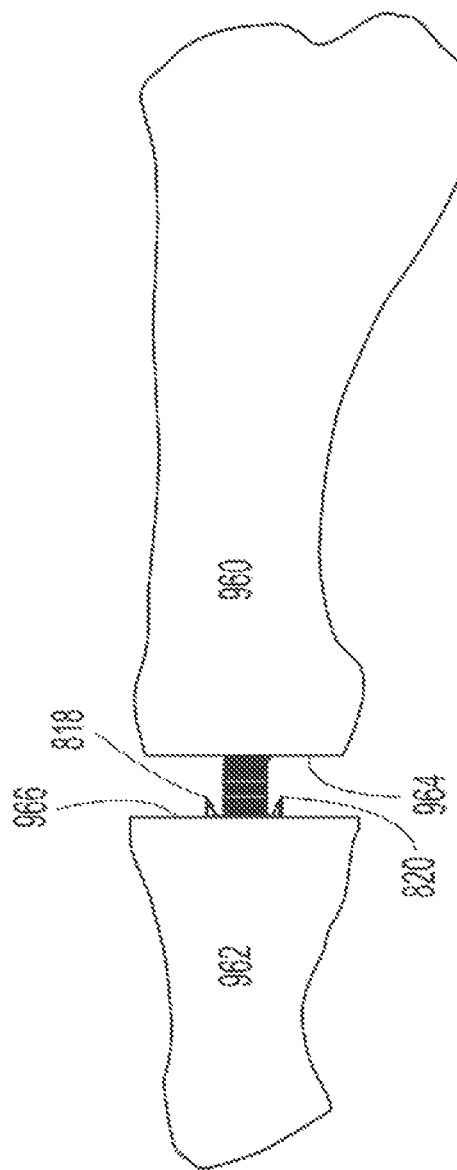

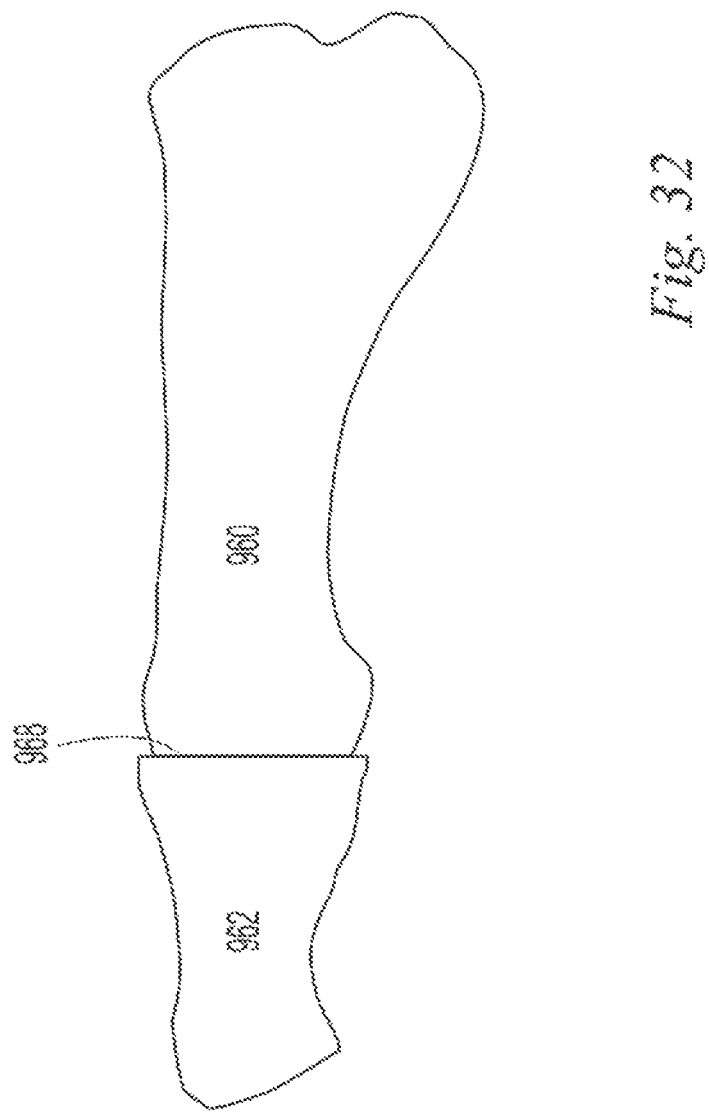

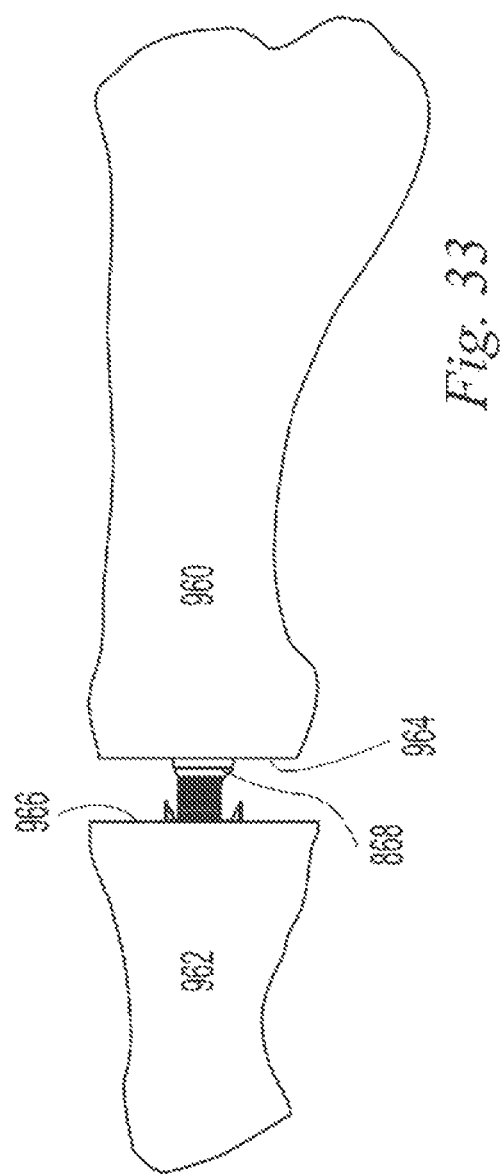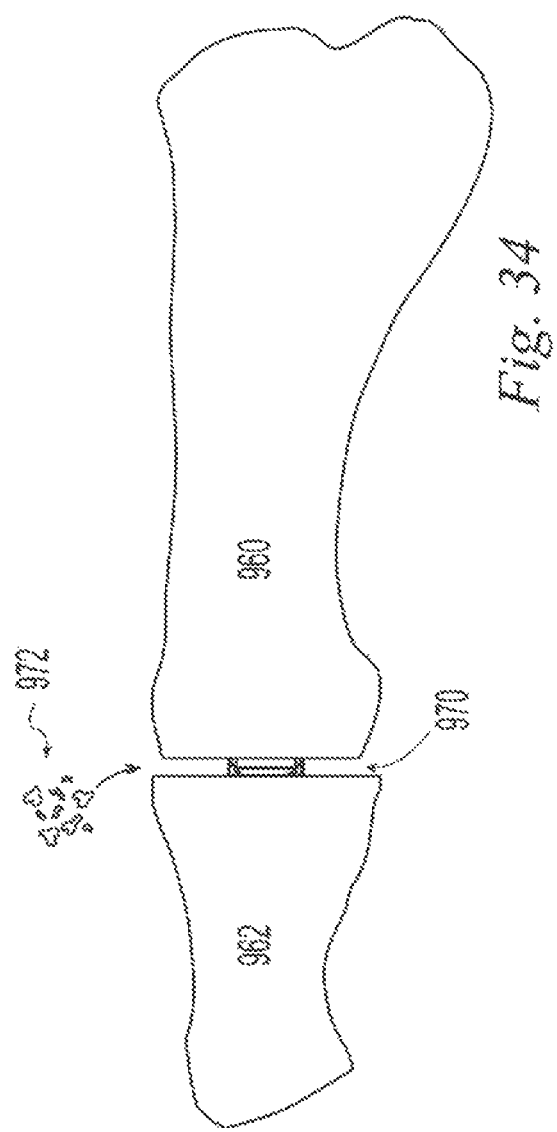

FUSION IMPLANT

CROSS-REFERENCE TO RELATED APPLICATIONS

This application is a divisional of U.S. patent application Ser. No. 13/845,544 filed Mar. 18, 2013 and issued as U.S. Pat. No. 10,631,994, which claims the benefit of U.S. Provisional Application No. 61/713,471 filed Oct. 12, 2012, the contents of each application hereby incorporated by reference in their entirety.

FIELD OF THE INVENTION

The invention relates to devices and methods for fusing bones, in particular the invention relates to devices and methods for fusing small bones such as for example the bone of the joints of the foot or hand.

BACKGROUND

Various conditions may affect skeletal joints such as the elongation, shortening, or rupture of soft tissues associated with the joint, arthritis, deformity, or other pathologies. Often fusion of the joint is the best treatment modality for the patient.

SUMMARY

The present invention provides devices and method for immobilizing adjacent bone portions to permit the bone portions to fuse together.

In one aspect of the invention, a fusion implant includes first and second components wherein the second component is operable to receive the first component in angularly constrained and press fit axial sliding relationship.

In another aspect of the invention, the fusion implant includes an intermediate portion comprising a plastic material.

In another aspect of the invention, a fusion implant includes first and second components wherein the second component includes a socket having a smooth inner wall and operable to receive the first component in infinitely adjustable axial sliding relationship.

In another aspect of the invention, a fusion implant includes first and second components wherein the second component is engageable with the first component and at least one of the first and second components includes at least one outwardly projecting anti-rotation member operable to engage bone surrounding the other component in torque transmitting relationship to resist rotation of the bone surrounding the other component relative to the anti-rotation member.

In another aspect of the invention, a method includes inserting a first end of a first component into a first bone with a second end of the first component projecting from the first bone; inserting a first end of a second component into a second bone adjacent the first bone, the second component having a second end including a socket, the socket having a smooth inner wall free of discrete axially spaced features; inserting the second end of the first component into the socket in infinitely adjustable axial sliding relationship; and adjusting the axial position of the first and second components by axially sliding the second end of the first component along the smooth inner wall of the socket to a desired axial position.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 16 is an exploded side elevation view of a component of the fusion implant of FIG. 2 and driver instrument useable with it;

FIG. 17 is a side elevation view of the component and instrument of FIG. 16;

FIG. 21 is a perspective view of an illustrative tapping instrument useable with the implants of the present invention;

FIG. 22 is a perspective view of an illustrative driving instrument useable with an implant component of FIGS. 2, 9, 14, and 19;

FIG. 23 is a perspective view of an illustrative driving instrument useable with an implant component of FIGS. 2, 15, and 18;

FIGS. 24-32 are side elevation views of a method of fusing bone portions using the implants and instruments of FIGS. 18-23; and FIGS. 33-34 are side elevation views of a variation of the method of FIGS. 24-32.

DESCRIPTION OF THE ILLUSTRATIVE EXAMPLES

The following illustrative examples illustrate devices and techniques for treating bones. Devices and techniques according to the present invention may be used in conjunction with any bone but the illustrative examples are shown in a size and form most suitable for the bones of the hand and foot. The hand and foot have a similar structure. Each has a volar aspect. In the hand the volar, or palmar, aspect includes the palm of the hand and is the gripping side of the hand. In the foot the volar, or plantar, aspect is the sole of the foot and is the ground contacting surface during normal walking. Both the hand and foot have a dorsal aspect opposite the volar aspect. Both the hand and foot include long bones referred to as metapodial bones. In the hand, the metapodial bones may also be referred to as metacarpal bones. In the foot, the metapodial bones may also be referred to as metatarsal bones. Both the hand and foot include a plurality of phalanges that are the bones of the digits, i.e. the fingers and toes. These phalanges include, for example, proximal phalanges that articulate with the metapodial bones, intermediate phalanges that articulate with the proximal phalanges, and distal phalanges that articulate with the intermediate phalanges. In both the hand and foot, each of the most proximal phalanges forms a joint with a corresponding metapodial bone. This joint includes a volar plate or band of connective tissue on the volar side of the joint. The joint, also includes collateral ligaments on the medial and lateral sides of the joint. A transverse ligament connects the heads of the metapodial bones. In the hand the joint is typically referred to as the metacarpophalangeal (MCP) joint having a pal mar plate on the palmar side, collateral ligaments medially and laterally, and a transverse ligament connecting the metacarpals. In the foot the joint is typically referred to as the metatarsophalangeal (MTP) joint having a plantar plate on the plantar side, collateral ligaments medially and laterally including proper collateral ligaments and accessory collateral ligaments, and a transverse ligament also known as the transverse metatarsal ligament. The joint between the proximal and intermediate phalanges is referred to as the proximal interphalangeal (PIP) joint and the joint between the intermediate and distal phalanges as the distal interphalangeal (DIP) joint. In the thumb and great toe there are only two phalanges.

For convenience, the illustrative examples depict the use of devices and techniques according to the present invention on bones associated with the PIP joints of the human foot. The illustrative instruments and techniques are also suitable for use on PIP joints of the human hand as well as at other joints and to fuse other bones, including bone fragments.

Figure 1:
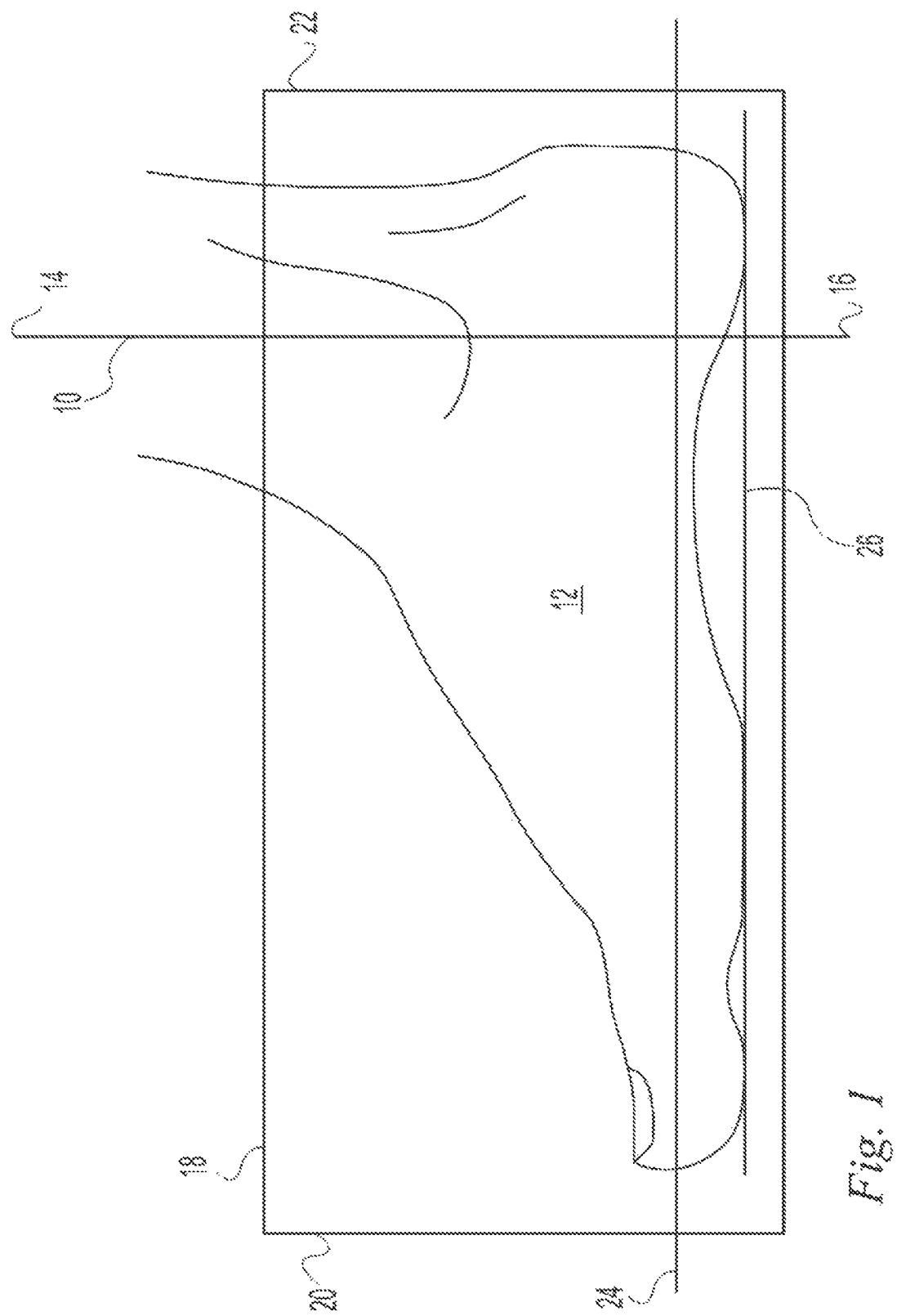
FIG. 1 is a side elevation view of the human foot illustrating anatomic reference planes.
Figure 2:
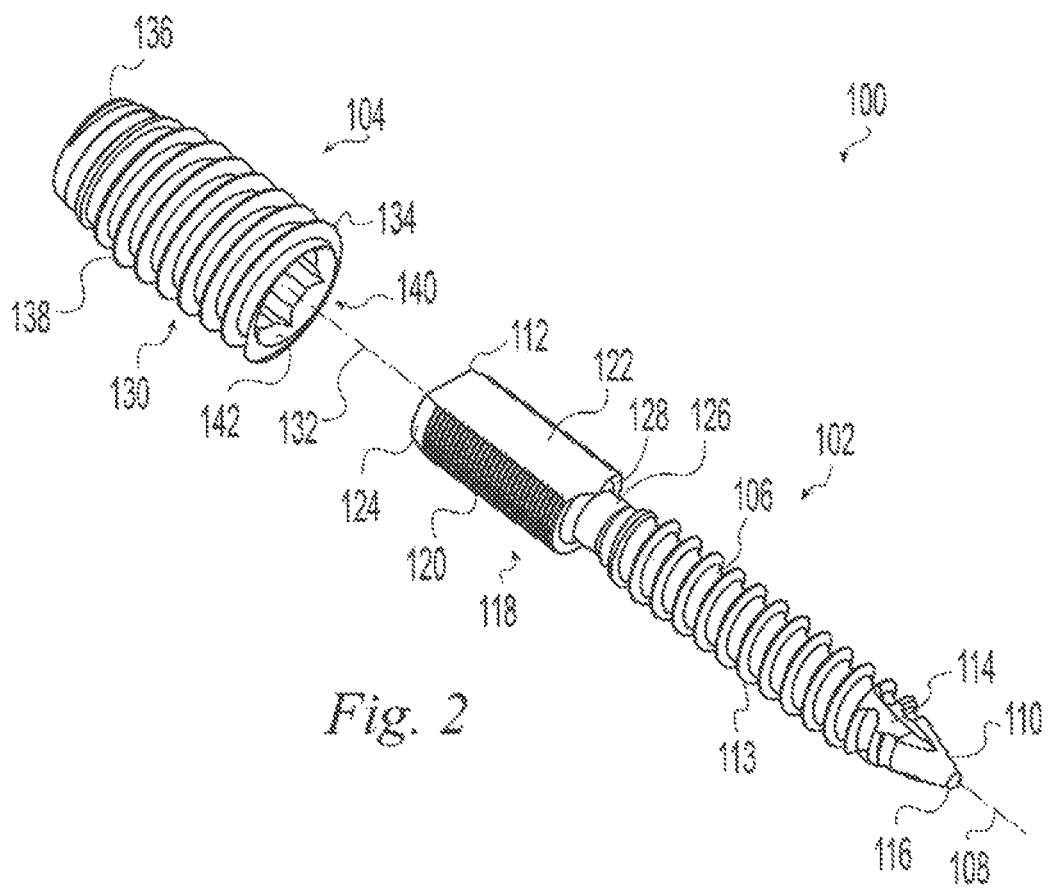
FIG. 2 is a perspective view of an illustrative example of a fusion implant according to the present invention.
Figure 3:
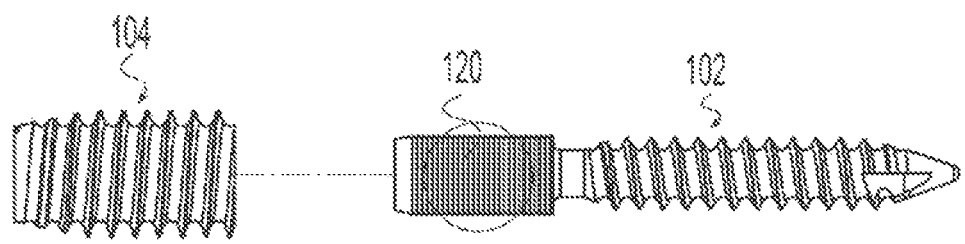
FIG. 3 is a side elevation view of the implant of FIG. 2.
Figure 4:
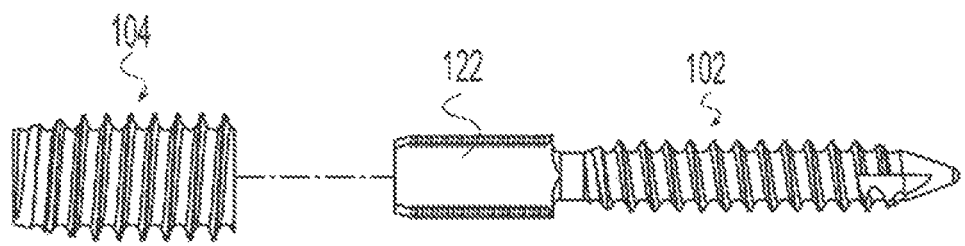
FIG. 4 is a top plan view of the implant of FIG. 2.
Figure 5:
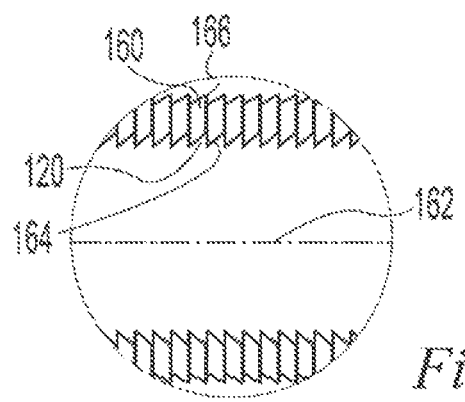
FIG. 5 is a detail view of the ridges on a component of the implant of FIG. 2 as shown in FIG. 3.

FIG. 1 illustrates the anatomic planes of the foot that are used for reference in this application. The coronal plane 10 extends from the medial aspect 12 to the lateral aspect of the foot and from dorsal 14 to plantar 16 and divides the foot between the toes and heel. The sagittal plane 18 extends anterior 20 to posterior 22 and dorsal 14 to plantar 16 and divides the foot into medial and lateral halves. The transverse plane 24 extends anterior 20 to posterior 22 and medial to lateral parallel to the floor 26.

FIGS. 2-5 illustrate an exemplary implant 100 useable to immobilize bone portions such as for example portions of a severed or broken bone to be fused or bones adjacent a skeletal joint that is to be fused. For example, the implant 100 may be used to fuse a PIP joint or a DIP joint of a human hand or foot. In the illustrative example of FIGS. 2-5, the implant includes first and second mating components 102, 104. The first component 102 includes an elongated body 106 defining a longitudinal axis 108 extending from a proximal end 110 to a distal end 112. External threads 113 extend over a portion of the body 106 from near the proximal end 110 toward the distal end 112 and include a self-tapping feature 114 able to cut threads as the component 102 is screwed into a bone. The proximal end 110 is also tapered to a point 116 to aid in starting threading the component into a bone. The point may also include drilling features if the bone is expected to be particularly dense. A head 118 is formed at the distal end 112. The head 118 is generally cylindrical and includes a plurality of ridges 120 projecting radially outwardly. A flat 122 is formed on one side of the head 18 to provide a driving surface for engagement with a driving instrument to rotate the implant. The flat 122 may also be sized to control the engagement area of the ridges 120 with the second component 104 to provide the desired fit with the second component 104. The distal end of the head 118 includes a chamfer 124 to provide a lead in to aid in engaging the first component 102 with the second component 104. Alternatively, the head may have an internal drive feature such as a polygonal cavity, groove, or other feature. An intermediate portion 126 of the body is positioned between the proximal and distal ends 110, 112. A shoulder 128 is formed at the proximal end of the head 118 at the transition from the relatively larger cross section of the head and the relatively smaller cross section of the intermediate portion 126.

The ridges 120 may have a variety of shapes including helical threads, discrete annular rings, rectangular in cross section, triangular in cross section, and/or any other suitable shape. Preferably, the ridges 120 project radially outwardly a sufficient distance to increase their flexibility to the point that they deform upon engagement with the second component and thereby ease insertion into the second component. The ridges preferably are resiliently biased into frictional engagement with the second component to resist withdrawal. The tightness of the compression fit between the components may also be tailored by controlling the overall area of the ridges such that, for example, providing the flat 122 reduces the area of the ridges and tends to ease insertion and extraction of the head. In the illustrative example of FIGS. 2-5, the ridges 120 are triangular in cross section as best seen in the detail view of FIG. 5. Each ridge 120 has a distal facing surface 160 that converges distally toward the longitudinal axis 162 of the head 118 forming an acute angle relative to the axis 162 and a proximal facing surface 164 that is approximately perpendicular to the longitudinal axis 162 of the head 118. The surfaces 160, 164 meet at a vertex 166. The angle of the distal surface 160 eases insertion of the head 118 into the second component 104. The angle of the proximal surface 164 resists extraction of the head 118 from the second component 104. During extraction, forces on the vertex 166 of each ridge tend to cause the ridge 120 to expand and increase the frictional engagement. The angle of the proximal surface 164 also causes the ridge to dig into the mating surface of the second component 104.

In the illustrative example of FIGS. 2-5, the head 118 has a unitary, solid construction without cantilevered prongs or internal features such as sockets and slots that could weaken the head 118.

The second component 104 of the illustrative example of FIGS. 2-5, includes an elongated body 130 defining a longitudinal axis 132 extending from a proximal end 134 to a distal end 136. The body 130 includes external threads 138 allowing the body 130 to be screwed into a bone. The body 130 includes an internal cavity 140 sized to receive the head 118 of the first component in a bi-directional, axial sliding, press fit relationship. In the illustrative example of FIGS. 2-5, the cavity 140 has an axially smooth inner wall that permits bi-directional axial translation of the head 118 within the cavity. Since there are not discrete positive engagement features in the cavity 140, the first and second components 102, 104 are infinitely adjustable in axial translation between the initial and final insertion positions. The bi-directional nature of the press fit permits the components to be pulled apart if desired to adjust the length of the fused bone portions or to remove the components, for example, to change to an alternate size or shape to better fit the patient or in a revision surgical procedure.

In the illustrative example of FIGS. 2-5, the cavity 140 also has a polygonal cross section, in this particular example it is hexagonal, that is able to receive a correspondingly shaped driver as well as the head 118 of the first component 102. A lead in chamfer 142 is provided to ease insertion of a driver and the head 118. The cavity 140 may extend part way through the body 130 such that it is only open at one end or it may extend completely through the body 130. In the illustrative example of FIGS. 2-5 the cavity extends through the body. Alternatively, an external drive feature such as one or more flats or grooves may be provided on the body.

The first and second components may be made of any suitable biocompatible material that will allow a press fit between the parts. For example, medical grade metals and metal alloys as well as the wide variety of medical grade plastics may be used. Plastics are particularly advantageous. In the illustrative example of FIGS. 2-5, the ridges 120 of the head 118 of the first component 102 and/or the cavity wall deform as the head is pressed into the cavity creating a frictional press fit that resists axial translation of the components. Plastics, being more easily deformed than typical implantable metals, provide a lower, more desirable axial translation force to facilitate insertion while providing an acceptably high extraction force. Furthermore, in addition to the compression fit, materials may be chosen to cause greater localized deformation of one of the components which may further increase the axial translation force. This may be enhanced by selecting a relatively hard material for one of the implant components and a relatively soft material for the other component. For example a metal component may be paired with a plastic component or materials of the same class but having different hardness may be paired such as a relatively hard plastic and a relatively soft plastic. It is preferable in such a pairing of relatively hard and relatively soft materials to make the female component of the softer material so it can deform around the ridges 120. For example, a low yield, high elongation to failure plastic may be used for the female component while a high yield plastic may be used for the male component as it provides a greater bias force against, and more deformation within, the female component. For example, polyetheretherketone may be used for the male component and polyethylene may be used for the female component. The invention is not limited to such relatively hard and relative soft pairings. It has been found that using the same high modulus plastic, such as for example polyetheretherketone, for both components works well.

Elastic deformation of the components may increase the extraction force necessary to separate the components. For example, elastic deformation may occur upon insertion of the first component 102 into the second component 104. With the ridge geometry of FIG. 5, the angled distal surface 160 eases insertion while the abrupt edge created by the vertex 166 and proximal surface 164 will tend to catch on the elastically deformed material upon extraction to increase the extraction force. Likewise, the parts may be sized and the materials chosen to create plastic deformation with a similar effect on the extraction force.

Components composed of plastics, or other relatively easily cut materials, are also advantageous in this application because such materials allow the components to be easily separated by cutting through the implant with readily available instruments in the operating environment such as scalpels, chisels, saws and other instruments. The entire first and/or second component, or selected portions, may be made of such a material. For example, the intermediate portion 126 of the first component 102 may be made of plastic to facilitate cutting through the first component 102 adjacent the head 118. This is advantageous, for example, where it is desired to remove the components, for example, to change to an alternate size or shape to better fit the patient or in a revision surgical procedure.

Suitable plastics may include polyethylenes, polyesters, aromatic ketones, and other biocompatible plastics. They may be resorbable or non-resorbable. The components may be machined, molded, or otherwise formed. The components may be provided in a range of sizes to allow the user to select an appropriate size for a particular patient. If the parts are made of a non-radiopaque material, they may include radio markers or radiopacifying additives.

Preferably, the first component is sized to be implanted into the more proximal phalanx and the second component is sized to be implanted into the more distal phalanx. The more proximal phalanx has a smaller intramedullary canal than the more distal phalanx. It is therefore advantageous to place the larger cross sectional area female component distally to maximize the size of the components and thus their strength to resist bending, shear, and torsion loads.

Figure 6:
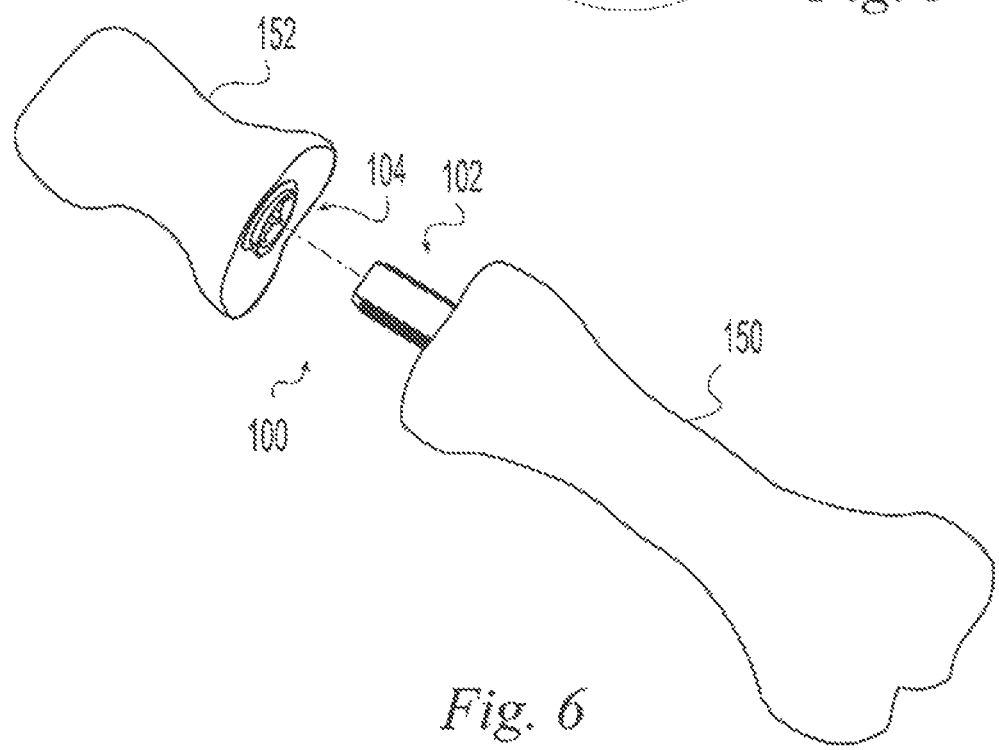
FIG. 6 is an exploded perspective view of the implant of FIG. 2 in use to fuse two bones.
Figure 7:
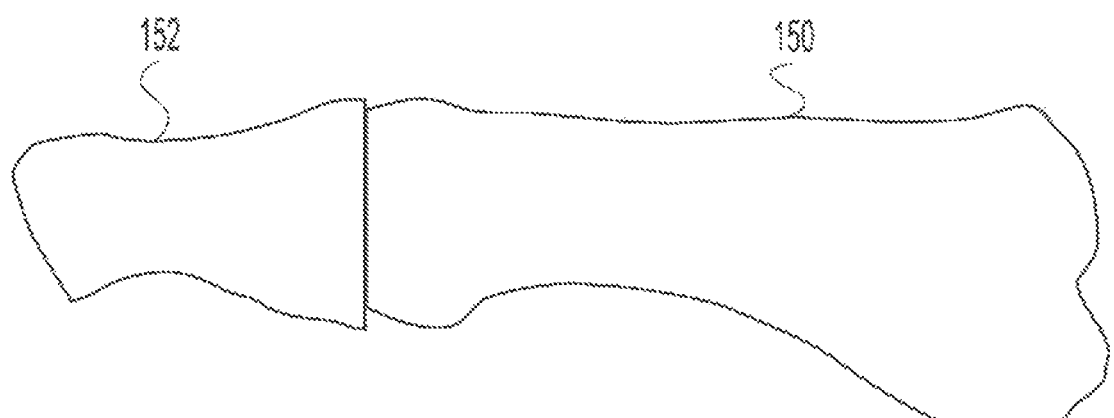
FIG. 7 is a side elevation view showing the bones of FIG. 6 fully reduced.

FIGS. 6 and 7 illustrate the implant 100 in use to fuse two bones. In the illustrative example of FIGS. 6 and 7, the bones of a PIP joint have been prepared by removing the articular cartilage from the articulating bone ends to produce flat bleeding bone surfaces able to be abutted in a desired degree of flexion/extension. The first component 102 has been threaded into the distal end of the proximal phalanx 150 with the head 118 extending distally beyond the bone. The second component 104 has been threaded into the proximal end of the intermediate phalanx 152. The head 118 of the first component is inserted into the cavity of the second component and the components are pressed into engagement in infinitely adjustable sliding relationship. The user stops translating the components when the bones are at a desired relative position. For example, the components may be pressed toward one another until the bones are reduced to abutting relationship. Alternatively, the user may stop when there is a gap between the bones and fill the gap with a bone graft substance. The implant 100 holds the bones relative to one another until they fuse. If needed, the bone can be separated by pulling the components apart so that they translate away from one another or by cutting through one or both components such as for example by passing a cutting instrument through or between one or both bones to cut one or both components.

Figure 8:
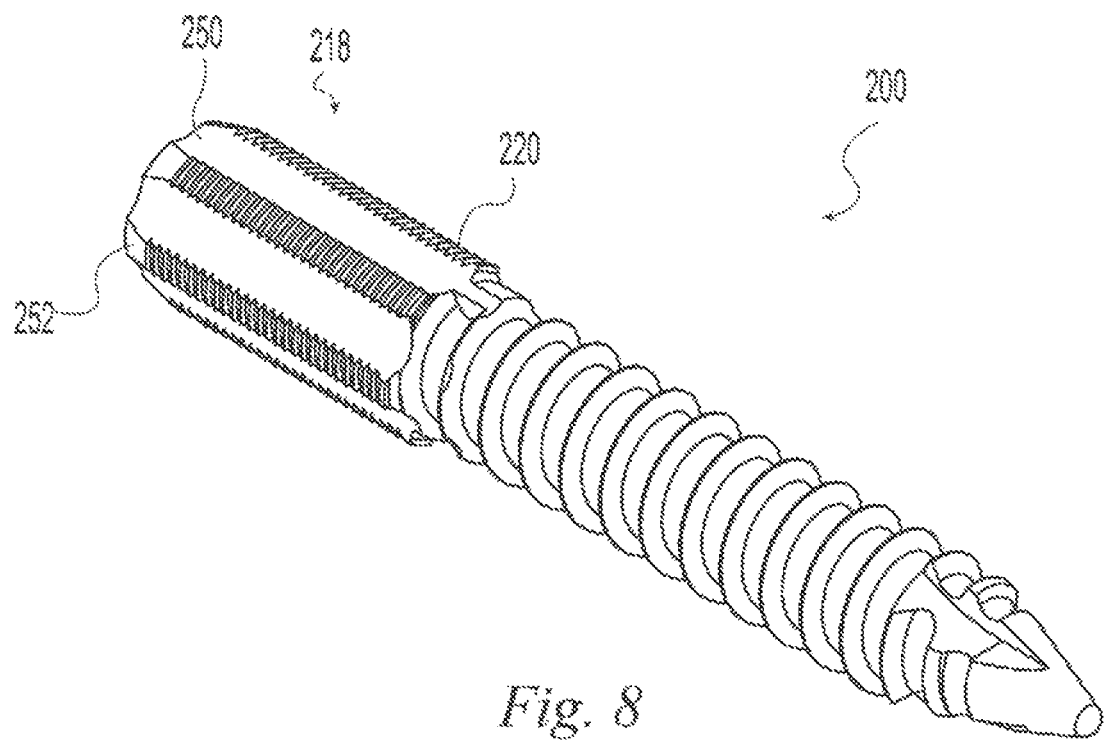
FIG. 8 is a perspective view an illustrative example of an alternative component of the fusion implant of FIG. 2.
Figure 9:
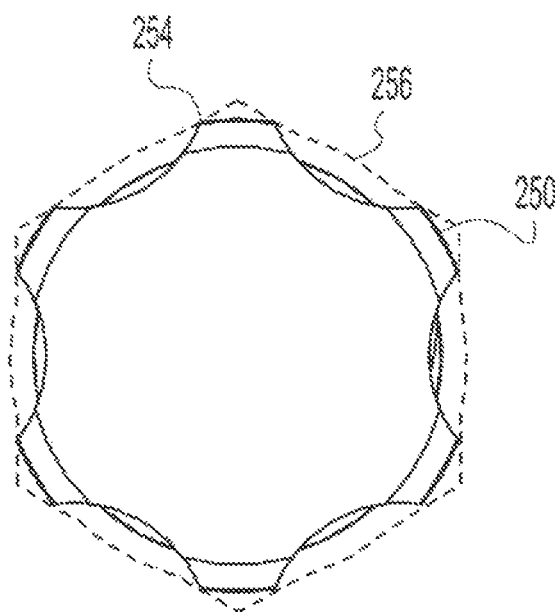
FIG. 9 is a rear elevation view of the component of FIG. 8.

FIGS. 8 and 9 illustrate an illustrative example of an alternative configuration of the first component. The component 200 includes a cylindrical head 218 having discrete annular ridges 220 similar to those of FIGS. 2-5. Flutes 250 have been formed lengthwise in the head 218 parallel to the longitudinal axis of the implant. The flutes 250 provide engagement with a driver for screwing the implant into a bone. The flutes 250 also define inter-flute lands 252 topped by the ridges 220. The intersections of the flutes 250 and lands 252 define corners 254. In the illustrative example of FIGS. 8 and 9, the component 200 has six lands 252 able to engage the six vertices of a hexagonal cavity 256. The corners 254 and contacting surfaces of the cavity may locally deform to increase the axial sliding force of the assembly. The land 252 and cavity 256 engagement also provides relative rotational constraint between the components since relative torque of the components would cause the land 252 to press against an adjacent cavity wall and prevent rotation.

Figure 10:
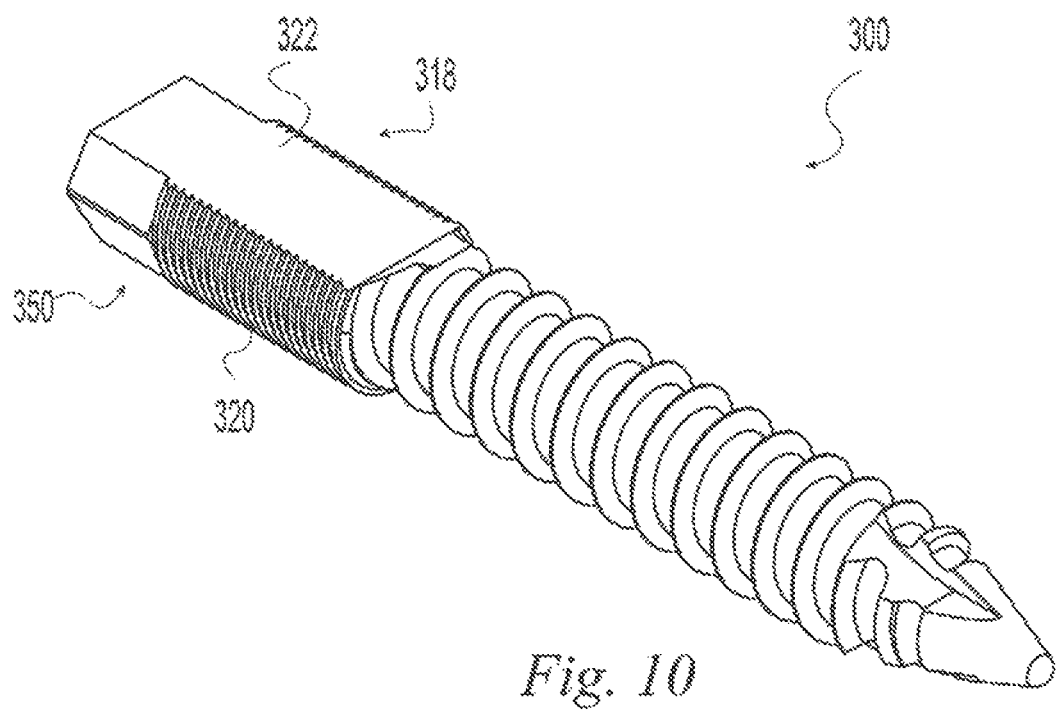
FIG. 10 is a perspective view an illustrative example of an alternative component of the fusion implant of FIG. 2.
Figure 11:
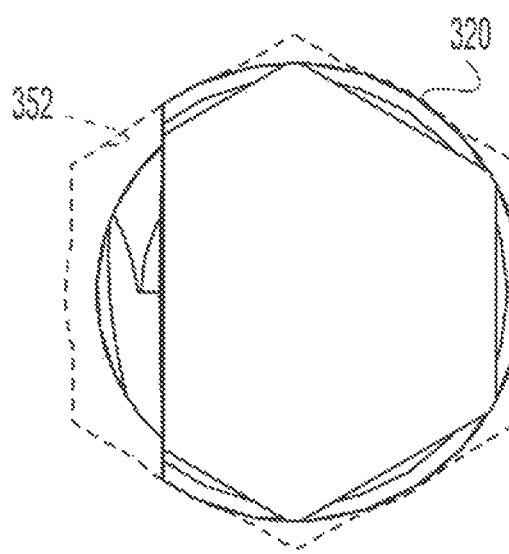
FIG. 11 is a rear elevation view of the component of FIG. 10.

FIGS. 10 and 11 illustrate an alternative configuration of the first component. The component 300 includes a cylindrical head 318 with ridges 320 and a polygonal extension 350 extending axially distally. The polygonal extension 350 may be shaped to complement a correspondingly shaped receiving cavity 352. In the illustrative example of FIGS. 10 and 11, the extension 350 and corresponding cavity 352 are hexagonal. The extension has a maximum dimension across the polygonal flats that is less than the outer diameter of the ridges 320 to provide clearance so that the deformable ridges are able to engage with a receiving cavity 352 and deform upon insertion into the cavity. The extension may provide a driving surface for screwing the component 300 into a bone. The extension also provides relative rotational constraint between the components. As the parts are rotated relative to one another the vertices of the polygonal extension will eventually abut the polygonal walls of the cavity 352 and prevent further rotation. Optionally, to provide a more robust driving surface, a flat 322 may be provided on the head.

Figure 12:
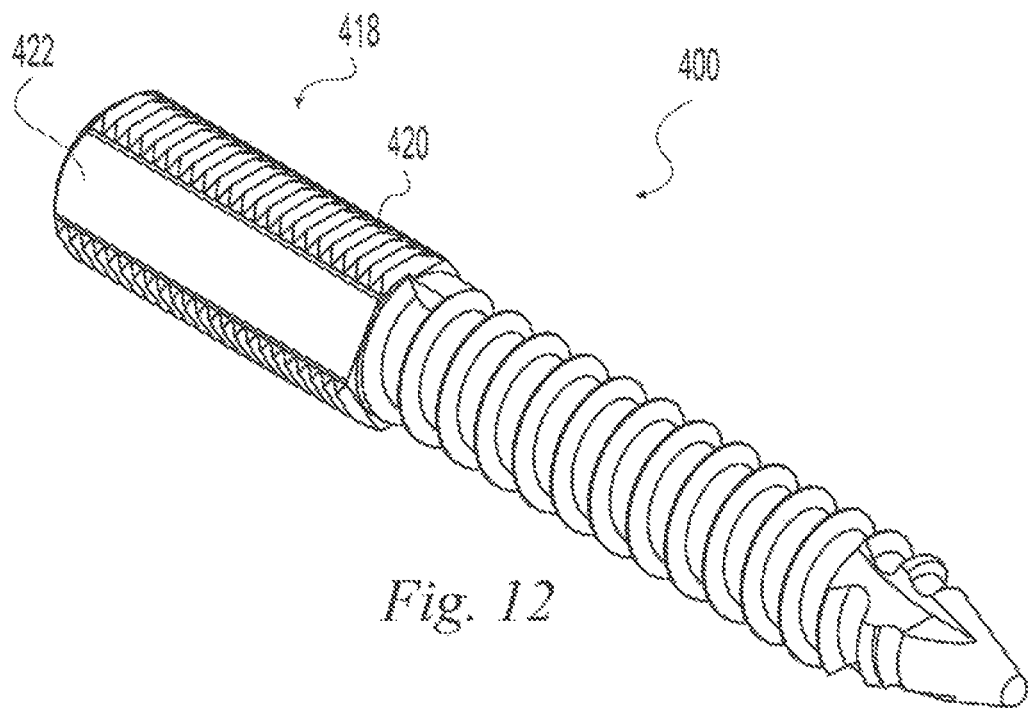
FIG. 12 is a perspective view an illustrative example of an alternative component of the fusion implant of FIG. 2.
Figure 13:
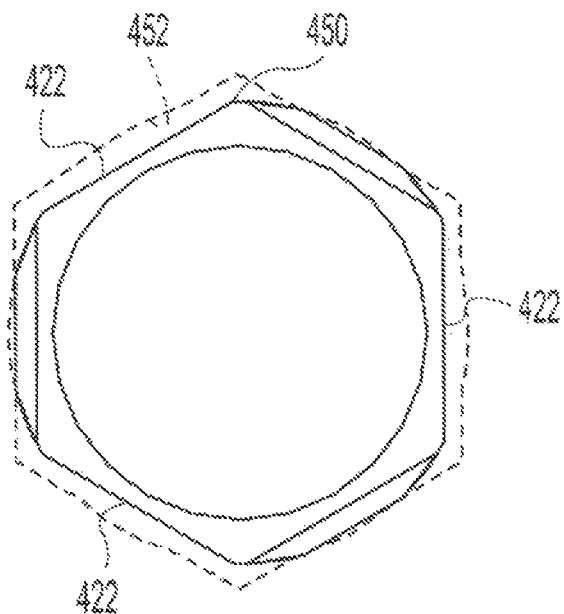
FIG. 13 is a rear elevation view of the component of FIG. 12.

FIGS. 12 and 13 illustrate an alternative configuration of the first component. The component 400 includes a cylindrical head 418 with ridges 420. Flats 422 have been formed on the head 418 to provide driving surfaces for screwing the component 400 into a bone. The flats 422 are arranged such that they provide relative rotational constraint between the components. As the parts are rotated relative to one another the corners 450 will eventually abut the polygonal walls of a receiving cavity 452 and prevent further rotation. In the illustrative example of FIGS. 12 and 13 there are three flats 422 and three ridged lands between them. The ridges 420 are also flat topped to increase the contact area with the walls of the cavity 452.

Figure 14:
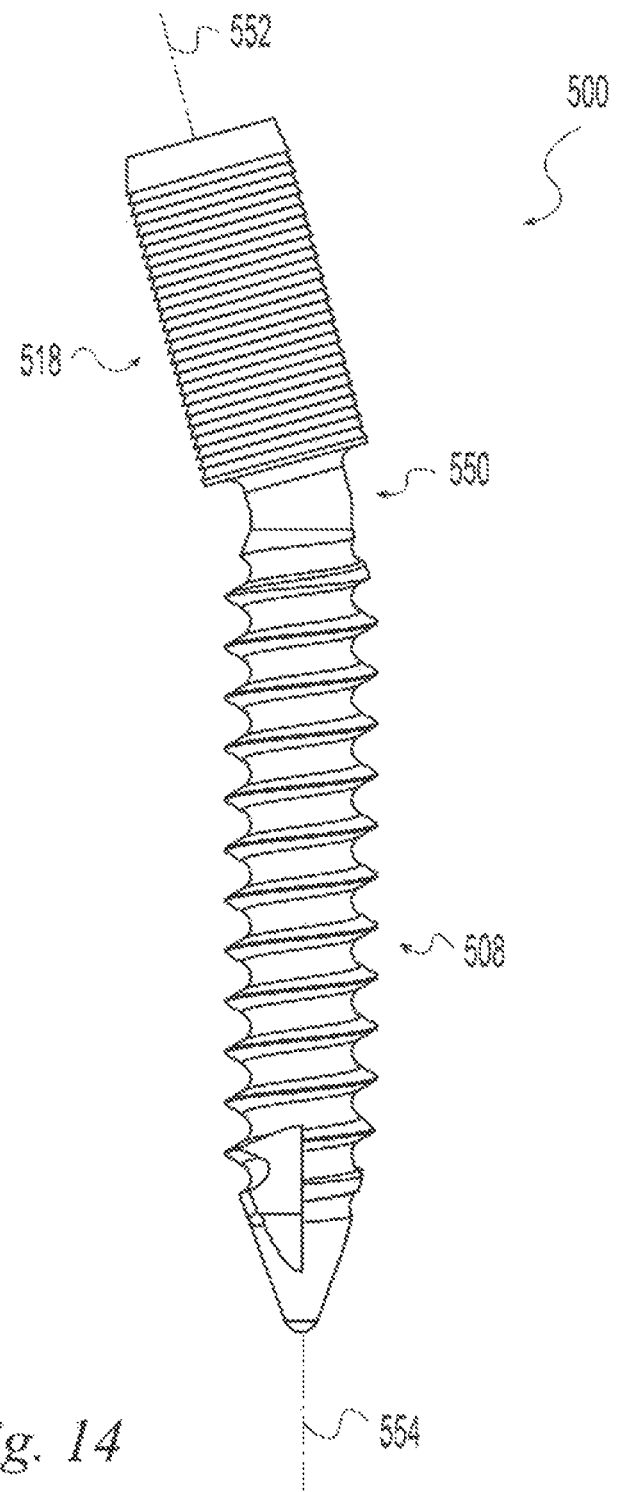
FIG. 14 is a side elevation view of an illustrative example of an alternative component of the fusion implant of FIG. 2.

FIG. 14 illustrates an alternative configuration of the first component. The component 500 has a bend 550 in an intermediate portion of the component angularly offsetting the head 518 from the rest of the body 508. The head includes a head axis 552 angled relative to the body axis 508. The component may be provided in a set of components having one or more angular offsets allowing the fused bones to be positioned in a desired angular relationship. For example, this may be useful in fusing phalangeal joints to set the digits in a desired degree of flexion for comfort and aesthetics.

Figure 15:
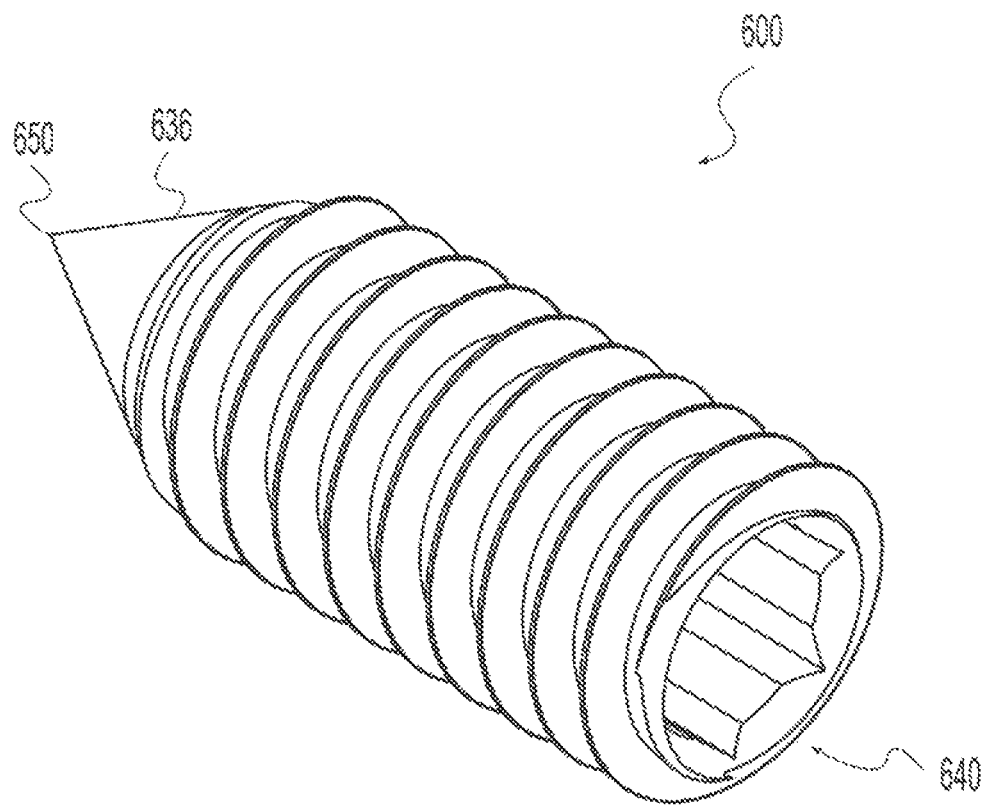
FIG. 15 is a perspective view an illustrative example of an alternative component of the fusion implant of FIG. 2.

FIG. 15 illustrates an alternative configuration of the second component. The component 600 has a closed distal end 636 forming a point 650 externally. The point 650 aids in starting the component 600 into a bone and may also be used to form an initial hole into which threads may be cut by optional self-drilling and/or self-tapping features of the implant. Furthermore, by closing the distal end, debris is prevented from entering the component 600 during insertion into a bone that might later interfere with engaging a male component with the cavity 640. In the illustrative example of FIG. 15, the closed distal end 636 provides more constraint and therefore less deformation toward the distal end of the cavity 640. As the first component is engaged with the cavity in axial sliding relationship, the insertion force increases with further distal translation and provides tactile feedback to the user.

FIGS. 16 and 17 illustrate a driver 700 useable with the second component 104 of FIGS. 2-5. The driver 700 includes a handle 702, a shaft 704, an engagement portion 706 and a distal point 708. In the illustrative example of FIGS. 15 and 16, the engagement portion 706 has a polygonal cross section engageable with a corresponding polygonal cross section in the component 104. The length of the engagement portion 706 and distal point 708 are arranged so that the distal point 708 extends beyond the component 104 when the component 104 is seated on the engagement portion 706. The point 708 aids in starting the component 104 into a bone and may also form an initial hole into which threads may be cut as the component 104 is driven. By arranging the engagement portion 706 and point 708 to fill the cavity in the component 104, debris is prevented from entering the component 104 during insertion into a bone that might later interfere with engaging a male component with the component 104.

Figure 18:
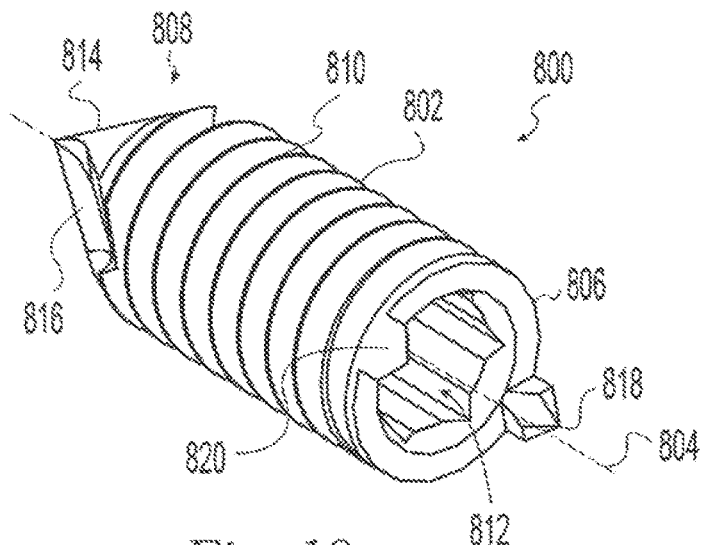
FIG. 18 is a perspective view an illustrative example of an alternative component of the fusion implant of FIG. 2.

FIG. 18 illustrates an alternative configuration of the second component similar to that of FIG. 15 but with additional features. The component 800 includes an elongated body 802 defining a longitudinal axis 804 extending from a proximal end 806 to a distal end 808. The body 802 includes external threads 810 allowing the body 802 to be screwed into a bone. The body 802 includes an internal cavity 812 sized to receive the head of the first component in a bi-directional, axial sliding, press fit relationship. The component 800 has a closed distal end forming a point 816 externally. The tip 816 includes a flute extending proximally into the threads 810 for a self-drilling and self-tapping configuration. A projection 818 extends proximally away from the proximal end 806 on portion of the body 802 spaced radially outwardly from the longitudinal axis 804. In the illustrative example of FIG. 18, the projection 818 is located on the circumference of the body 802 outside of the cavity 812. The projection 818 tapers proximally to a sharp point to enable it to penetrate into an opposing bone portion. The projection 818 keys the component 800 to the opposing bone portion in rotationally fixed relationship. Any number of projections 818 may be provided. In the illustrative example of FIG. 18, a second projection 820 is provided opposite the first projection 818 and they form of a pair of radially opposed proximally extending anti-rotation prongs.

Figure 19:
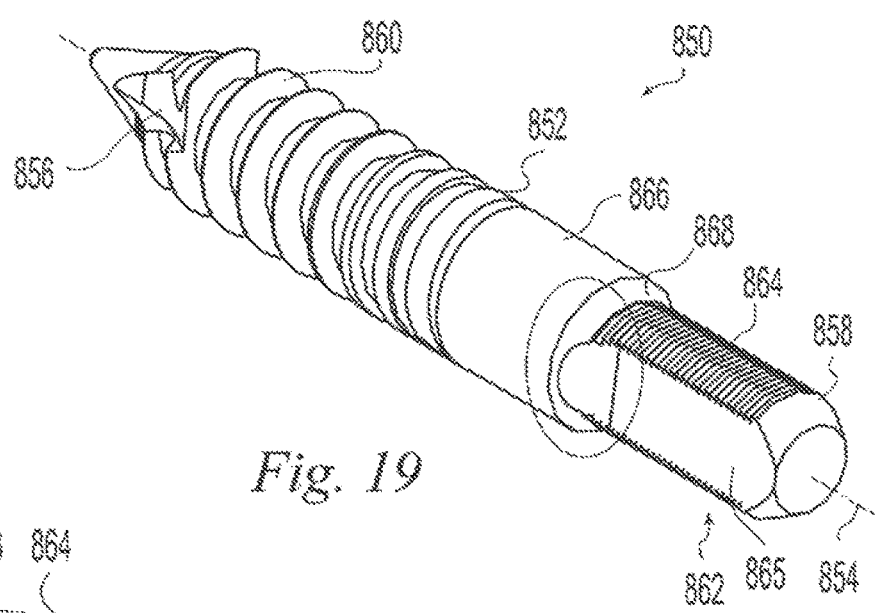
FIG. 19 is a perspective view an illustrative example of an alternative component of the fusion implant of FIG. 2.

FIGS. 18-19 illustrate an alternative configuration of the first component similar to that of FIGS. 2-5. The component 850 includes an elongated body 852 defining a longitudinal axis 854 extending from a proximal end 856 to a distal end 858. External threads 860 extend over a portion of the body 852 from near the proximal end 856 toward the distal end 858. A head 862 is formed at the distal end 858. The head 862 is generally cylindrical and includes a plurality of ridges 864 projecting radially outwardly. A flat 865 is formed on one side of the head 862 to provide a driving surface for engagement with a driving instrument to rotate the implant. An intermediate portion 866 of the body is positioned between the proximal and distal ends 856, 858. A shoulder 868 is formed at the distal end of the intermediate portion 866 at the transition from the relatively larger cross section of the intermediate portion and the relatively smaller cross section of the head. The shoulder tapers distally from the intermediate portion 866 to the head 862.

Figure 20:
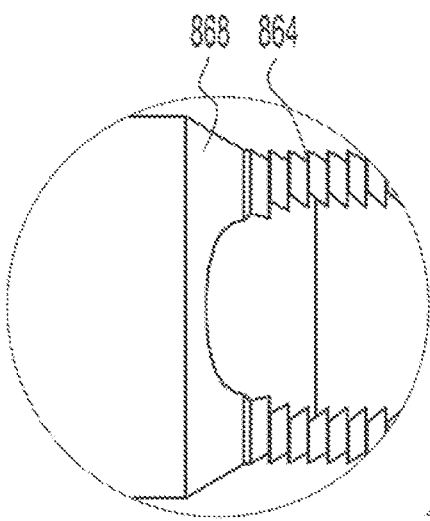
FIG. 20 is a detail view of the ridges on the component of the implant of FIG. 19.

FIGS. 21-23 depict an illustrative example of a set of instruments in use with the implants of FIGS. 17-19. FIG. 20 illustrates a tap assembly 900 including a handle 902 and a modular tap 904 having a thread forming portion 906. Modular taps 904 may be provided in a range of sizes corresponding to different sizes of the first and second components 850, 800 and being interchangeable within the handle 902. FIG. 21 illustrates a driver 920 having a handle 922 and a shaft 924 engageable with the first component 850. In the illustrative example of FIG. 22, the shaft has a D-shaped passage 926 able to engage the head of the first component 850 in torque transmitting relationship. FIG. 22 illustrates a driver 940 having a handle 942 and a shaft 944 engageable with the second component 800. In the illustrative example of FIG. 23, the shaft has a projecting polygonal end 946 able to engage the cavity of the second component 800 I torque transmitting relationship. The shaft 944 includes relieved portions 948, 950 that receive the projections 818, 820 on the proximal end of the second component 800 and allow the second component to fully engage the driver. Alternatively, the second component 800 may have a circular cavity and the projecting end 946 of the driver shaft 944 may also be circular with torque transmission being via the projections 818, 820 and relieved portions 948, 950.

FIGS. 23-32 depict a technique for fusing two bone portions. In the illustrative technique of FIGS. 23-32, the implants and instruments of FIGS. 18-23 are shown in use to fix a proximal and intermediate phalanx of a PIP joint in order to fuse the joint.

Figure 24:
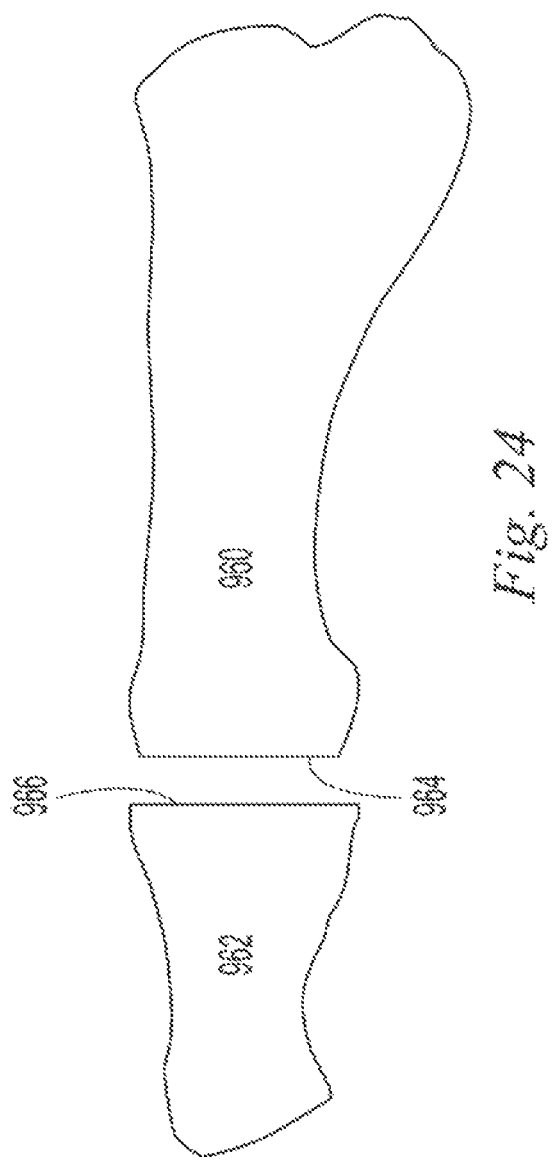

In FIG. 24, articulating ends of the proximal phalanx 960 and intermediate phalanx 962 have been cut to provide flat fusion surfaces 964, 966.

Figure 25:
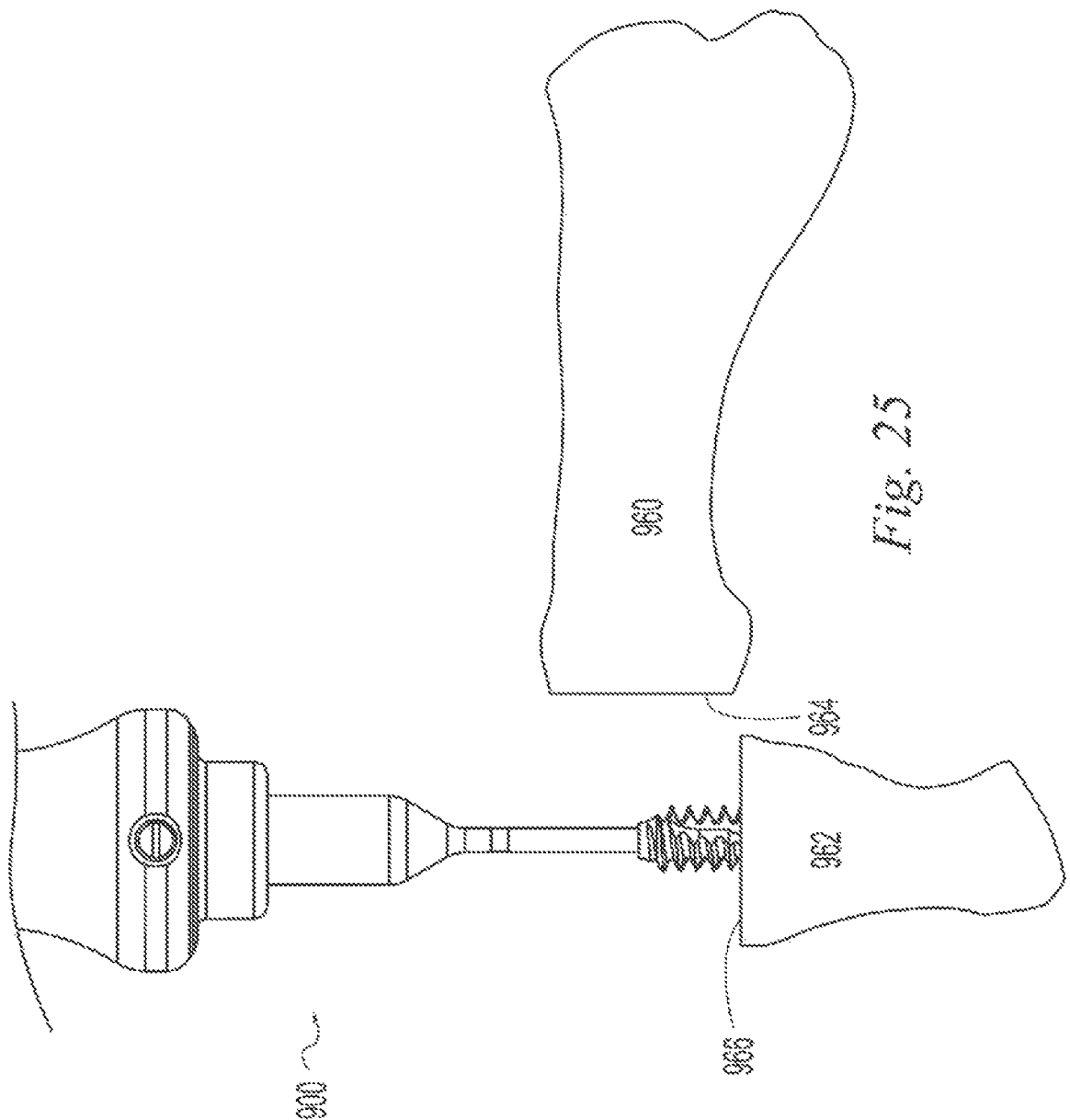

In FIG. 25, the phalanges have been placed in flexion and the tap assembly 900 is shown in use tapping the intermediate phalanx 962 proximally to distally in preparation for receiving the second component 800.

Figure 26:
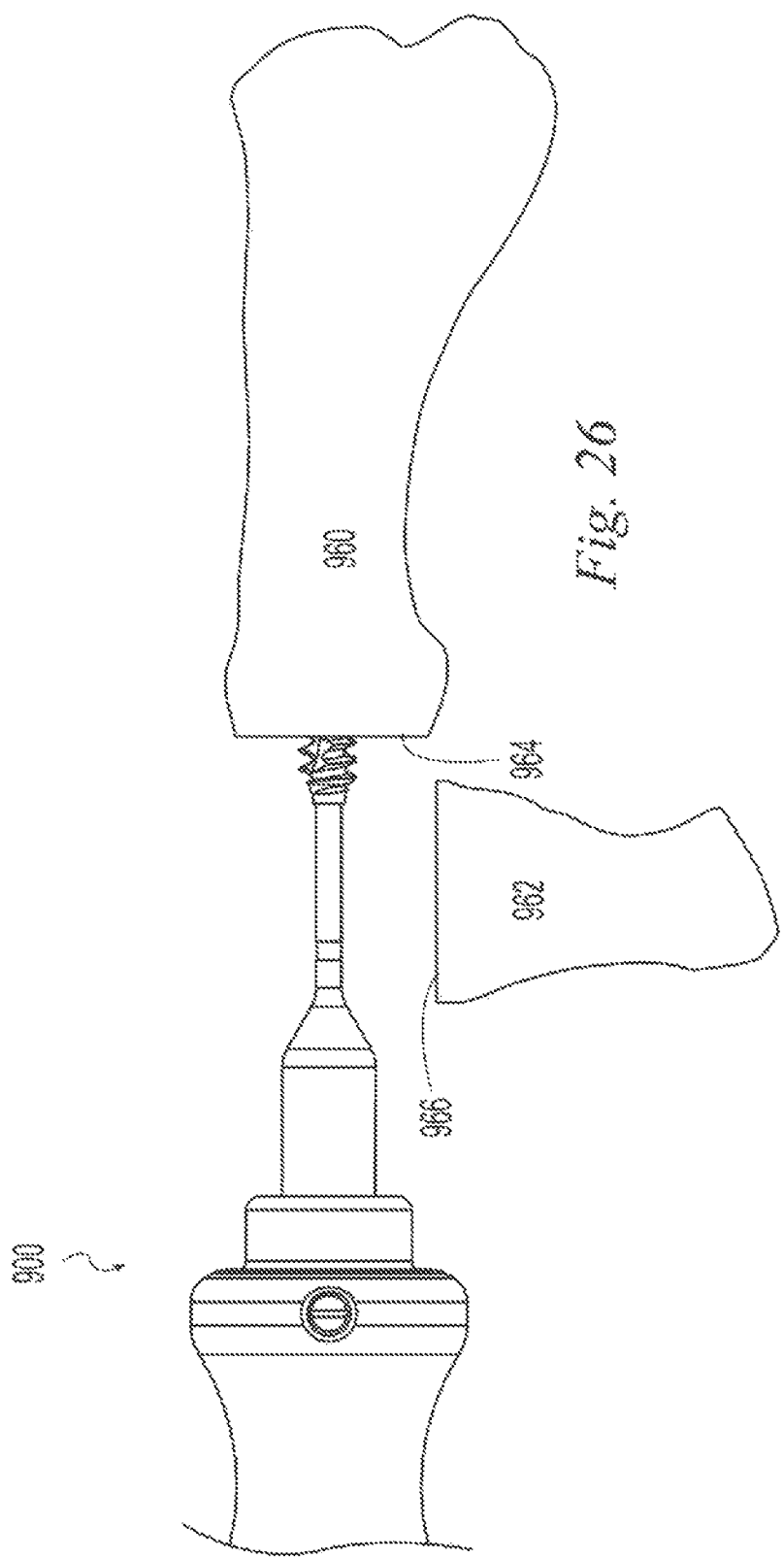

In FIG. 26, the tap assembly 900 is shown in use tapping the proximal phalanx 960 distally to proximally in preparation for receiving the first component 850.

Figure 27:
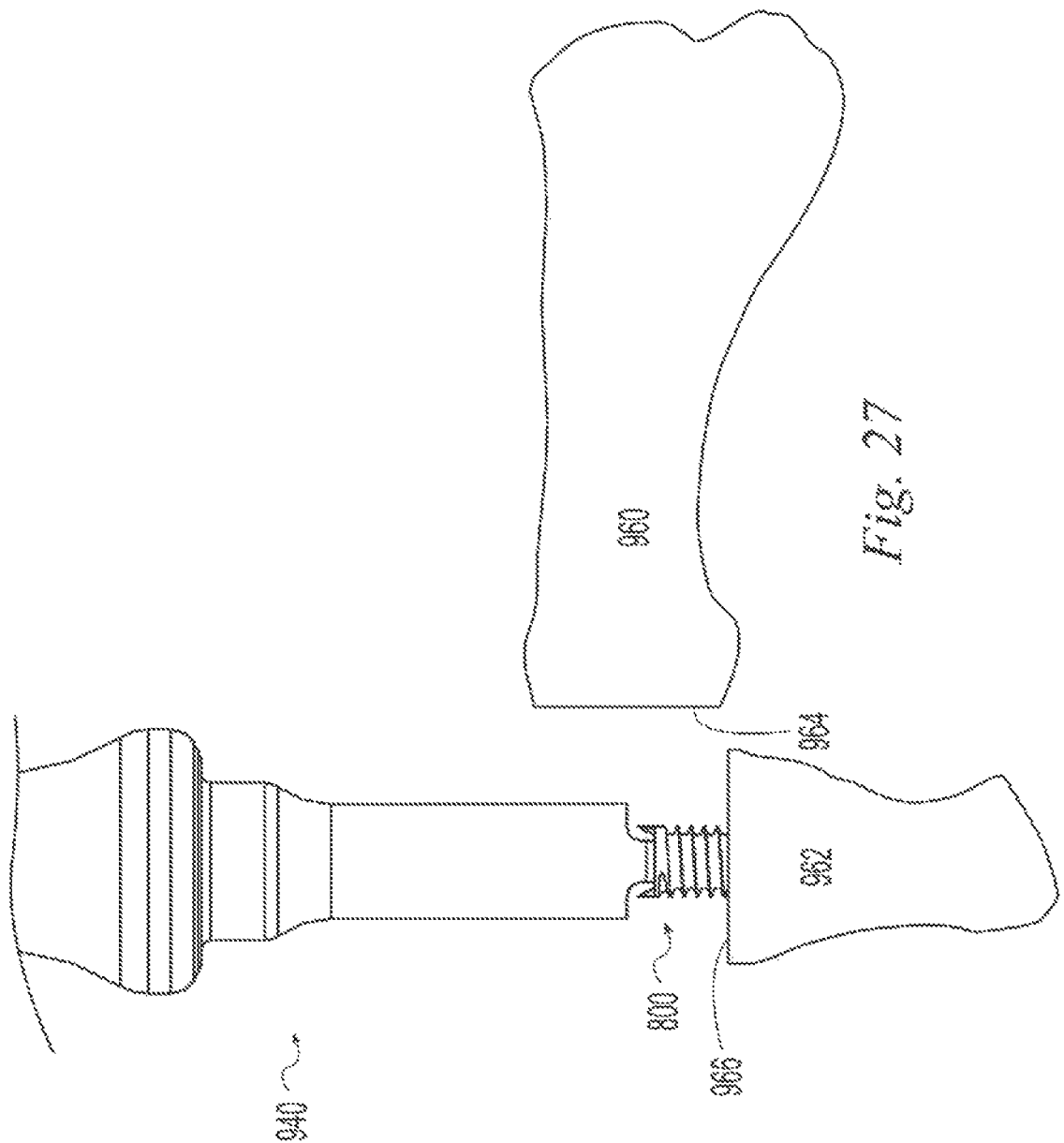

In FIG. 27, the driver 940 is shown in use driving the second component 800 into the intermediate phalanx 962.

Figure 28:
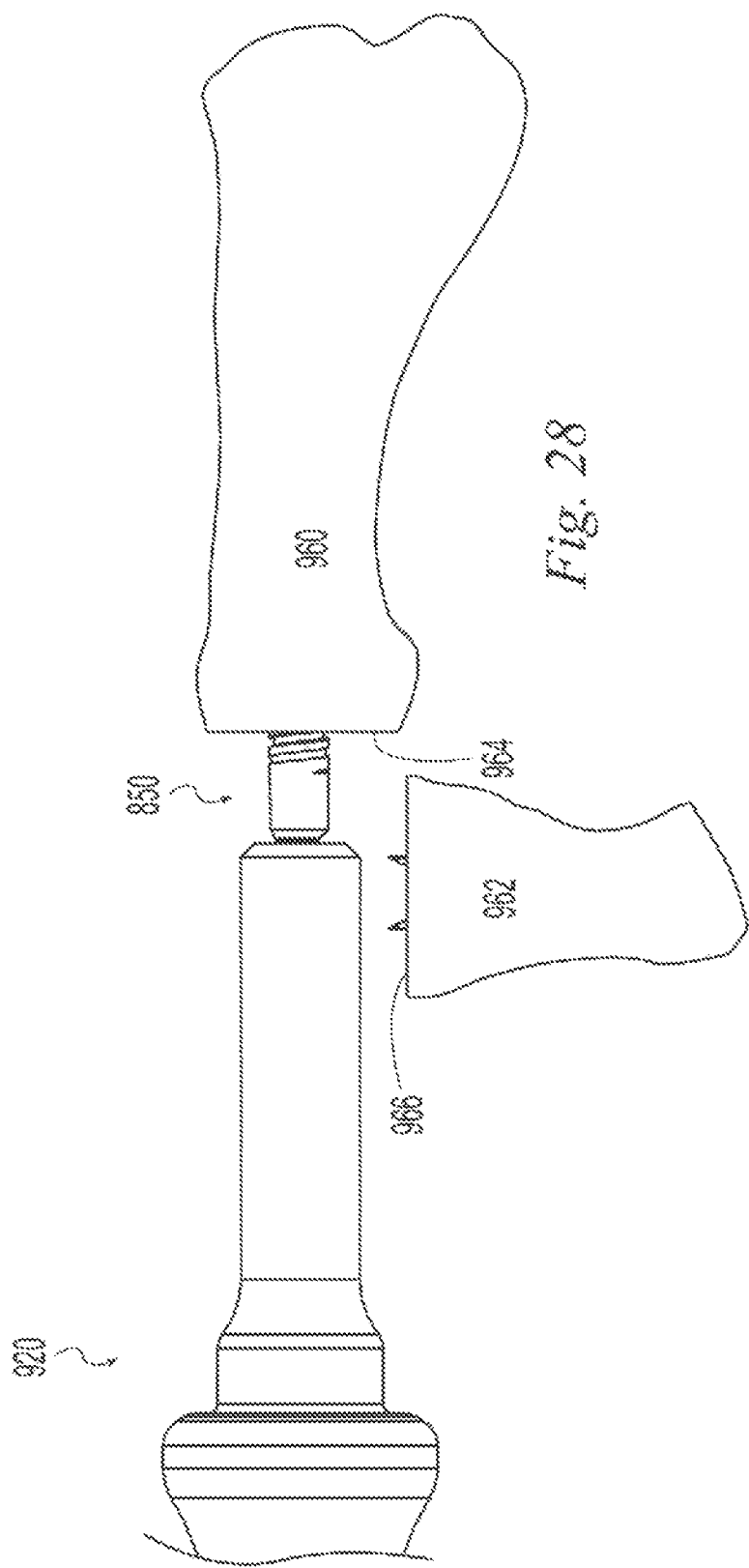

In FIG. 28, the driver 920 is shown in use driving the first component 850 into the proximal phalanx 960.

Figure 29:
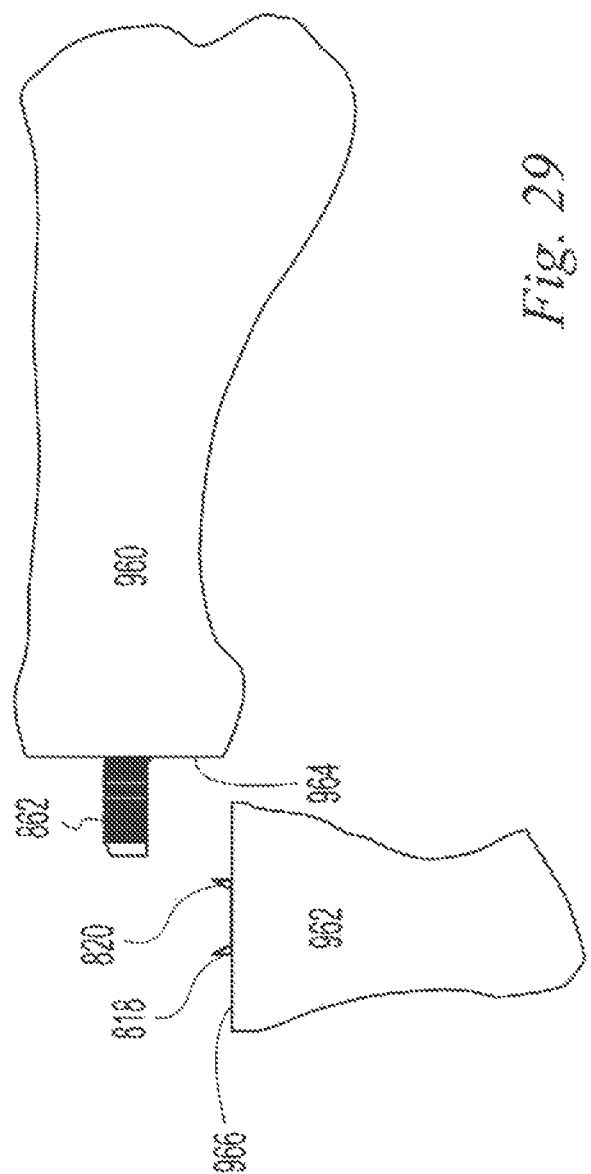

FIG. 29 depicts the bones and components prior to reduction of the bones. The second component 800 has been set at or below flush with the cut surface 966 of the intermediate phalanx 962 with the projections 818, 820 extending proximally beyond the cut surface 966 so that they are able to engage the cut surface 964 of the proximal phalanx 960. The first component 850 has been set with the shoulder 868 at or below flush with the cut surface 964 of the proximal phalanx 960 with the head 862 extending distally beyond the cut surface 964 so that it can engage the cavity 812 of the second component 800.

Figure 30:
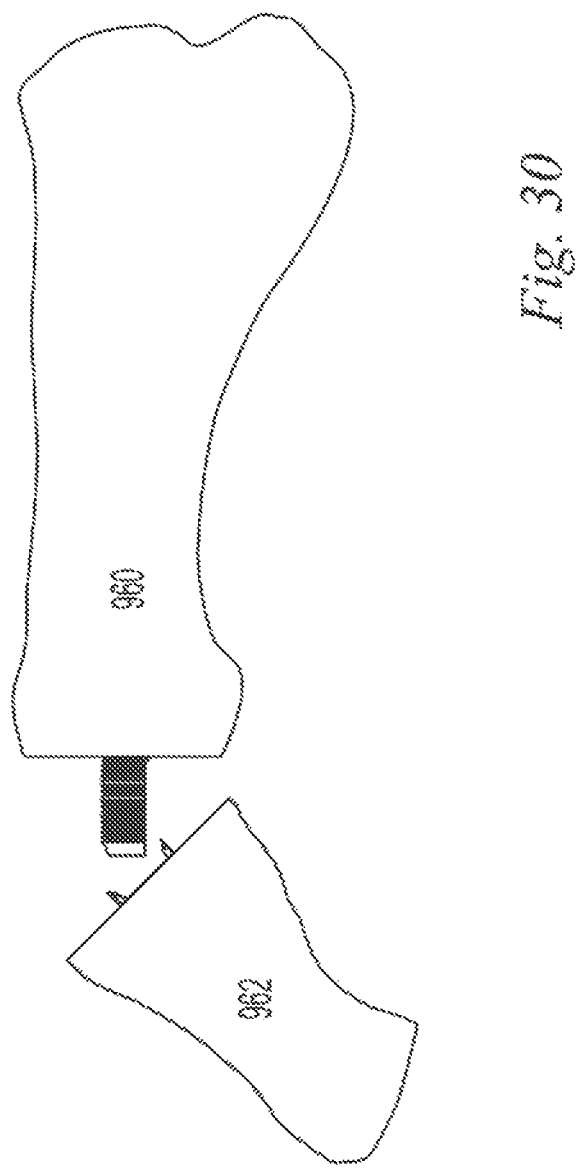

FIG. 30 illustrates the bones 962, 960 in process of being extended and reduced.

FIG. 31 illustrates the head 862 of the first component 850 initially engaging the cavity 812 of the second component 800. The components, and bones, may now be pressed toward one another in infinitely adjustable bi-directional axial sliding relationship to a desired spacing between the cut ends 964, 966. If desired, the components can be pulled apart or advanced together as needed. The projections 818, 820 of the second component 800 may be pressed into engagement with the cut surface 964 of the proximal phalanx to provide rotational constraint to the reduced bone.

In FIG. 32, the bones have been fully reduced with the projections 818, 820 embedded in the cut surface 964 of the proximal phalanx and the cut surfaces 964, 966 abutting at a joint line or interface 968.

FIGS. 33 and 34 depict an alternative technique in which the shoulder 868 of the first component 850 is left proud of the cut surface 964 of the proximal phalanx 960 to create a space 970 between the bone ends such as for example when it is desirable to restore the original length of the uncut bone portions or to lengthen the bones. The proximal end 806 of the second component 800 abuts the shoulder 868 to provide a positive stop to the engagement of the first and second components 850, 800. Bone graft material 972 may then be placed in the space 970 between the bones to facilitate fusion.

The illustrative implants and instruments have been shown in use to fuse a PIP joint. However, the implants and instruments may be used to fix other joints and bone portions other than at joints. The illustrative implant components have been shown with threads for engaging the bone portions. However, it is within the scope of the invention to provide the bone components with other features for engaging the bone portions or the components may be free of such features. For example, the bone engaging portion of the components may include other types of engaging surfaces such as spikes, ridges, barbs, knurling, blasted surfaces, bone ingrowth surfaces or smooth surfaces. The illustrative examples have shown the male implant component positioned in a proximal phalanx and the female implant component positioned on the intermediate phalanx due to the relative sizes of the bones and the desire to maximize the cross-sectional area of the components. However, it is within the scope of the invention to reverse the placement of the components.

What is claimed is:

1. A method of fusing a bone joint, the method comprising:
   inserting a first end of a first component into a first bone with a second end of the first component projecting from the first bone;
   inserting a first end of a second component into a second bone adjacent the first bone, the second component having a second end including a socket, the socket having a smooth inner wall free of discrete axially spaced features;
   inserting the second end of the first component into the socket in a continuously adjustable axial press-fit sliding relationship between the second end of the first component and the smooth inner wall of the socket; and
   adjusting the axial position of the first and second components by axially sliding the second end of the first component along the smooth inner wall of the socket to a desired axial position.

2. The method of claim 1, further comprising:
   separating the first and second components by axially sliding the first and second components apart.

3. The method of claim 1, wherein at least one of the first and second components includes a polymer portion, the method further comprising:
   separating the first and second components by cutting through the polymer portion.

4. The method of claim 1, wherein at least one of the first and second components includes at least one outwardly projecting anti-rotation member, the method further comprising:
   engaging the at least one anti-rotation member with the bone surrounding the other of the first and second components in a torque transmitting relationship to resist rotation of the bone surrounding the other of the first and second components relative to the anti-rotation member.

5. The method of claim 1, wherein adjusting the axial position of the first and second components comprises adjusting the first and second components to leave a space between the first and second bones, the method further comprising:
   placing bone graft material in the space between the two bones.

6. A method, comprising:
driving a first end portion of a first component into a first bone such that a second end portion of the first component projects from the first bone, wherein the second end portion comprises a plurality of axially-spaced ridges;
driving a second component into a second bone such that a socket of the second component faces the second end portion of the first component, wherein the socket comprises a smooth inner wall;
inserting the second end portion of the first component into the socket, thereby engaging the plurality of axially-spaced ridges with the smooth inner wall of the socket in a sliding press fit arrangement; and
adjusting a relative axial position of the first component and the second component, wherein the sliding press fit arrangement retains the first component and the second component in the relative axial position without the use of discrete positive engagement features.

7. The method of claim 6, wherein the second end portion of the first component comprises a first flat operable to engage a corresponding second flat of a driver.

8. The method of claim 7, wherein the second end portion of the first component has a D-shaped cross-section.

9. The method of claim 7, further comprising:
prior to driving the first end portion of the first component into the first bone, attaching the driver to the second end portion by engaging the first flat with the second flat to enable transmission of torque between the driver and the first component; and
wherein driving the first end portion of the first component into the first bone comprises rotating the first component by rotating the driver.

10. The method of claim 6, wherein the socket has a polygonal geometry.

11. The method of claim 10, further comprising:
prior to driving the second component into the second bone, attaching a driver to the second component by inserting a portion of the driver into the socket to enable transmission of torque between the driver and the second component; and
wherein driving the second component into the second bone comprises rotating the second component by rotating the driver.

12. The method of claim 6, wherein the first end portion and the second end portion of the first component extend along a single longitudinal axis.

13. The method of claim 6, wherein the first bone is a first bone of a digit of a human hand or foot, and wherein the second bone is a second bone of the digit of the human hand or foot.

14. A method, comprising:
driving a first component into a first bone, wherein the driving of the first component comprises rotating the first component by rotating a first driver engaged with a head of the first component in a first torque transmitting engagement;
removing the first driver from engagement with the head of the first component;
driving a second component into a second bone, wherein the driving of the second component comprises rotating the second component by rotating a second driver engaged with a polygonal socket of the second component in a second torque transmitting engagement;
removing the second driver from engagement with the socket of the second component;
inserting the head into the socket such that a continuously-adjustable, press-fit, axially-sliding arrangement is formed between the first component and the second component; and
adjusting a relative axial position of the first component and the second component, and wherein the continuously-adjustable, press-fit, axially-sliding arrangement maintains a selected relative axial position of the first component and the second component.

15. The method of claim 14, further comprising attaching the first driver to the head of the first component, and wherein the attaching the first driver to the head of the first component comprises inserting the head into the first driver such that a first flat of the head engages a second flat of the first driver.

16. The method of claim 15, wherein the head has a D-shaped cross-section.

17. The method of claim 14, further comprising attaching the second driver to the second component, wherein the attaching the second driver to the second component comprises inserting a polygonal end of the second driver into the polygonal socket of the second component.

18. The method of claim 14, further comprising engaging an axial projection formed on one of the first component and the second component with bone surrounding the other of the first component and the second component, thereby discouraging relative rotation of the first bone and the second bone.

19. The method of claim 14, wherein the continuously-adjustable, press-fit, axially-sliding arrangement maintains the selected relative axial position of the first component and the second component without the use of discrete positive engagement features.

20. The method of claim 14, wherein the adjusting the relative axial position of the first component and the second component comprises adjusting the relative axial position of the first component and the second component through a continuous range of relative axial positions, and—wherein the continuously-adjustable, press-fit, axially-sliding arrangement is configured to maintain each relative axial position throughout the continuous range of relative axial positions.

* * * * *